US005358712A

United States Patent [19]

Efange et al.

[11] Patent Number: 5,358,712

[45] Date of Patent: Oct. 25, 1994

[54] RADIOPHARMACEUTICAL AGENTS FOR THE DETECTION OF ALZHEIMER'S DISEASE

[75] Inventors: Simon M. Efange, Plymouth, Minn.; Stanley M. Parsons, Santa Barbara, Calif.

[73] Assignee: Regents of the University of Minnesota, Minneapolis, Minn.

[21] Appl. No.: 117,736

[22] Filed: Sep. 8, 1993

Related U.S. Application Data

[63] Continuation of Ser. No. 668,967, Mar. 13, 1991, abandoned.

[51] Int. Cl.[5] .................... A61K 43/00; A61K 49/02; C07F 13/00

[52] U.S. Cl. .................................. 424/1.65; 424/1.85; 534/10; 534/14

[58] Field of Search ...................... 424/1.1, 1.65, 1.85; 534/10, 14; 544/394, 372, 379; 546/205, 208, 212, 213, 240

[56] References Cited

U.S. PATENT DOCUMENTS 4,522,965 11/1985 Parsons .............................. 546/206
5,077,035 12/1991 Wieland et al. ...................... 424/1.1

OTHER PUBLICATIONS

"Mouse Brain Distribution of a Carbon-11 Labeled Vesamicol Derivative . . . " by Kilbourn et al., Life Sci., vol. 47, pp. 1955-1963, 1990.

"Acyclic Analogues of 2-(4-Phenylpiperidino) Cyclohexanol (Vesamicol)": . . . by Efange et al., *J. Med. Chem.*, vol. 34, pp. 2638-2643, 1991.

Brittain et al., 1969, *European Journal of Pharmacology*, vol. 8, pp. 93-99.

Brittain et al., 1969, British Pharmacology Society Proceedings, "Observations on the Neuromuscular Blocking Action". . . .

Reisine et al., 1978, *Brain Research*, vol. 159, pp. 477-481.

Rossor et al., 1982, *Brain* vol. 105, pp. 313-330.

Bowen et al., 1983, *Journal of Neurochemistry*, vol. 41, pp. 266-272.

Mountjoy et al., 1984, *Brain*, vol. 107, pp. 507-516.

Marien et al., 1987, *Proceeding of National Academy of Science*, vol. 84, pp. 876-880.

Marshall and Parsons, 1987, *Tins*, vol. 10, pp. 174-177.

Altar et al., 1988, *Synapse*, vol. 2, pp. 486-493.

Kaufman, et al., 1988, *Molecular Pharmacology*, vol. 36, pp. 452-458.

Rogers et al., 1989, *Journal of Medicinal Chemistry*, vol. 32, pp. 1217-1230.

Rogers and Parsons, 1990, *Neuroreport*, vol. 1, No. 1, pp. 22-25.

Jung et al., 1990, *J. Med. Chem.*, vol. 33, pp. 2065-2068.

Efange et al., "The Cholinergic Synaptic Vesick". . . , *Proceedings of the 37th Annual Meeting of the Society of Nuclear Medicine*, #37S, vol. 31, No. 5, May, 1990.

Jung et al., "Presynaptic Cholinergic Marker", *Proceedings of the 37th Annual Meeting of the Society of Nuclear Medicine*, #374, vol. 31, No. 5, May, 1990.

Rogers et al., "Synthesis, in Vitro Acetylcholine-Storage-Blocking Activities, and Biological Properties of Derivatives and Analogues of trans-2-(4-Phenylpiperidino) Cyclohexanol(Vesamical)", J. Med. Chem., 32(6), 1989, pp. 1217-1230.

Hanson, R. N. , *Int. J. Nucl. Med. Biol.*, "Radioiodinated 1-Sub-4-Phenylpiperazines as Potential Brain Imaging Agents", V. 12(4), 1985, pp. 315-320.

*Primary Examiner*—Robert L. Stoll
*Assistant Examiner*—Lara E. Chapman
*Attorney, Agent, or Firm*—Vidas, Arrett & Steinkraus

[57] ABSTRACT

Novel anticholinergics which are related to vesamicol are particularly useful when radiolabeled for evaluating cholinergic innervation in the living human brain. The cholinergic deficit in the Alzheimer's brain should be identifiable with these radioligands.

6 Claims, 8 Drawing Sheets

A B C

X= O, NH (dl)-Vesamicol

1 R = R' = H
2 R = $NH_2$ , R' = H.
2a R = H , R' = $NH_2$.
3 R = *I , R'=H.

4

5

7

9

10

11

12

13

A B C

X= O, NH (-)-4-($^{125}$I) HIPP
3 HR 19 17 18

16 15 n= 0,1
X= CH, N

VESAMICOL

1b

1 : R = R' = H
2 : R = $NH_2$ ; R' = H
2a: R = H ; R' = $NH_2$
3 : R = I ; R' = H

4 : R = H
14 : R = $CH_3$

15 & 16
X = CH, N

15g

15h

15i

RADIOPHARMACEUTICAL AGENTS FOR THE DETECTION OF ALZHEIMER'S DISEASE

This invention was made with government support under grant NS-15047 awarded by the National Institute of Health. The Government has certain right:s in this Invention.

This application is a continuation of Ser. No. 07/668,967, filed Mar. 13, 1991, abandoned.

BACKGROUND OF THE INVENTION

1. Field of the Invention

This invention relates to a chemical compound that is an anticholinergic. This compound may be labeled and used to track brain nerve cell production of acetylcholine as an indicator of Alzheimer's disease.

2. Description of the Related Art

In U.S. Pat. No. 4,522,965 which issued Nov. 12, 1985 to Stanley M. Parsons, a vesamicol derivative is described for use in blocking conduction at the neuromuscular junction in mammals. Parsons notes that it is desirable to produce a more effective compound than vesamicol for blocking presynaptic release of acetylcholine.

The hydroxylated phencyclidine (PCP) isomer trans-2-(4-phenylpiperidino)cyclohexanol (vesamicol, AH5183) induces respiratory paralysis and death in rodents and other laboratory animals (Brittain et al., 1969). Subsequent investigations have revealed that the biological activity of vesamicol is mediated in part by its ability to inhibit both the uptake of ACh into cholinergic synaptic vesicles and quantal release of this neurotransmitter from cholinergic neuron (for review, see Marshall and Parsons, 1987).

Vesamicol has the ability to inhibit both the uptake of ACh into cholinergic synaptic vesicles and quantal release of this neurotransmitter from cholinergic neuron. Vesamicol binds reversibly to a unique cytoplasmically-oriented site, the vesamicol receptor, located on the cholinergic synaptic vesicle (and the prejunctional neuronal membrane) and thus interferes with the aforementioned processes. Given its location, the vesamicol receptor may be a useful presynaptic marker of cholinergic innervation. Such a receptor site would provide a suitable target for the development of radiotracers for mapping cholinergic pathways in vivo.

The study of cholinergic innervation in vivo is potentially of diagnostic value in neurodegenerative disorders such as Alzheimer's disease wherein significant decreases in cholinergic innervation have been detected early in the disease progression (Reisine et al 1978; Rossor et al 1982; Bowen et al 1983; Mountjoy et al 1984). The potential utility of the vesamicol receptor as a presynaptic cholinergic marker has been demonstrated by preliminary characterization of [$^3$H]vesamicol binding in the rodent brain (Marien et al 1977; Altar et al 1988). In these studies, the distribution of radiolabelled vesamicol was found to correlate well with other markers of cholinergic innervation. In addition, a significant decrease in cortical [$^3$H]vesamicol binding was obtained by lesioning a known cholinergic pathway (Altar et al 1988; Marien et al 1987).

Alzheimer's disease (AD) is a progressive neurodegenerative disorder associated with loss of memory and other cognitive functions. Recent epidemiologic studies suggest that 10% of adults over the age of 65 (about 4 million people) may suffer from this disorder.

Progress in the diagnosis and subsequent clinical management of AD has been slowed by the absence of both a reliable diagnostic procedure and an established therapeutic regimen. Currently, a definitive diagnosis of AD can only be made by histopathologic examination of brain tissue. Brain biopsy is not practical in clinical practice. Therefore, patients are subjected to a battery of psychometric, radiologic and chemical tests designed to exclude the presence of other diseases. Only 50% of these diagnoses are found to be accurate at autopsy.

An important feature of AD is that neurons which produce the neurotransmitter acetylcholine (cholinergic neurons) progressively degenerate. More importantly, the extent of this degeneration correlates with the severity of AD. Biochemical markers of cholinergic innervation could be used as reliable indicators of AD. The anticholinergic vesamicol binds selectively to a unique site (the vesamicol receptor) on the cholinergic synaptic vesicle, and thus inhibits the uptake of acetylcholine into the synaptic vesicle.

Radiolabeled ligands for the vesamicol receptor will be clinically useful radiopharmaceuticals for evaluating cholinergic innervation in the living human brain. In conjunction with SPECT, these radioligands which bind selectively to the vesamicol receptor should identify the cholinergic deficit in the Alzheimer's brain.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

In view of the foregoing, it was considered useful to develop a radioiodinated vesamicol analog as a potential radiopharmaceutical for use with Single Photon Emission Computed Tomography (SPECT). One such analog, 3 of FIG. 1, has recently been reported (Jung et al 1990). Radioiodinated (−)-3 exhibits significant vesamicol-sensitive accumulation in the rodent brain. In addition, (−)-[$^{125}$I]3 showed prolonged retention and high levels in the rodent cortex and striatum; the accumulation in the cerebellum was minimal. In contrast to the levorotary antipode, (+)-[$^{125}$I]3 exhibited rapid efflux from the rodent brain, clearly demonstrating enantioselectivity by the vesamicol receptor.

As noted by Parsons, vesamicol is not effective in lower concentrations and would dissociate too quickly from the receptor to be a good radiopharmaceutical. The Parsons compound of U.S. Pat. No. 4,552,965 does not meet the objectives outlined herein.

In earlier structure-activity studied (Kaufman et al 1988; Rogers et al 1989), a number of useful trends were discerned. Notably the vicinal aminoalcohol functionality was found to be important for vesamicol-like inhibitory activity. Replacement of the cyclohexyl moiety with a tetrahydronaphthyl group yielded potent analogs such as 1 and 2 suggesting that the "benzo" fragment was tolerated by the vesamicol receptor. In contrast, substitution for the cyclohexyl moiety with two- or three-carbon fragments yielded the weak inhibitors 4 and 14 suggesting a 'minimum steric bulk' requirement for this region of the receptor. Such a requirement may be attributed to essential nonbonded hydrophobic interactions within this region of the receptor. Based on the foregoing observations, we postulated a) that the minimum, bioactive fragment at the vesamicol receptor is represented by 14*a* and *b*) that simple analogs of 2 which satisfy the steric requirement at the vesamicol receptor would be potent ligands for this receptor site.

Although analogs of the benzovesamicol subclass (e.g. 2 and 3) are potent ligands for this receptor, positional isomers of disparate biological activity (e.g. 2 and 2*a*) are obtained during the synthesis of the desired compounds (Rogers et al 1989). In addition, the eudesmic ratio of these conformationally restricted analogs such as 1 and 3 is not unity, precluding the use of racemates. Thus, 2*a* must be separated from 2 and the latter in turn must be resolved to yield the active analog (−)-2. Based on these considerations, it was deemed necessary to develop a structurally and/or stereochemically simple vesamicol analog for radiotracer development. The desired stereochemically simple molecule would exhibit:

a) facile blood brain barrier penetrability;

b) selective and high affinity binding to the vesamicol receptor with minimal nonspecific binding;

c) significant metabolic stability in vivo; and d) slow dissociation from the receptor.

Following analysis of the available structure-activity data (Kaufman et al 1988; Rogers et al 1989), the secobenzovesamicol, 5 (also referred to as 4-HIPP), was proposed as a simple structure that would satisfy the stereoelectronic demands of the vesamicol receptor.

The invention provides the secobenzovesamicol, 5, and other analogs of vesamicol which meet the objectives outlined above. The compounds of the invention have the following chemical structure:

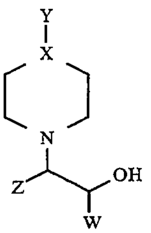

wherein

X is CH, N;

Y is an aromatic, heteroaromatic or alicyclic group;

Z is H, or an arylalkyl, heteroarylalkyl, aroylalkyl, heteroaroylalkyl, cycloalkyl, or aryl group, any of which groups may be substituted;

W is H, or an arylalkyl, heteroarylalkyl, aroylalkyl, heteroaroylalkyl, cycloalkyl, or aryl group, any of which groups may be substituted. Either Z or W may be a chelating group.

These compounds may be radiolabeled and used as reliable targets for radiotracer development. Additionally, since the compounds of the invention are anticholinergics, they may be used where anticholinergics are desired, such as in pesticides or muscle relaxants. The radiolabel may be a transition metal or any acceptable tag which will make the compound detectable outside the brain.

BRIEF DESCRIPTION OF THE DRAWINGS

A detailed description of the invention is hereafter described with specific reference being made to the drawings in which.

DESCRIPTION OF THE PREFERRED EMBODIMENTS

Chemistry

Figure 4:
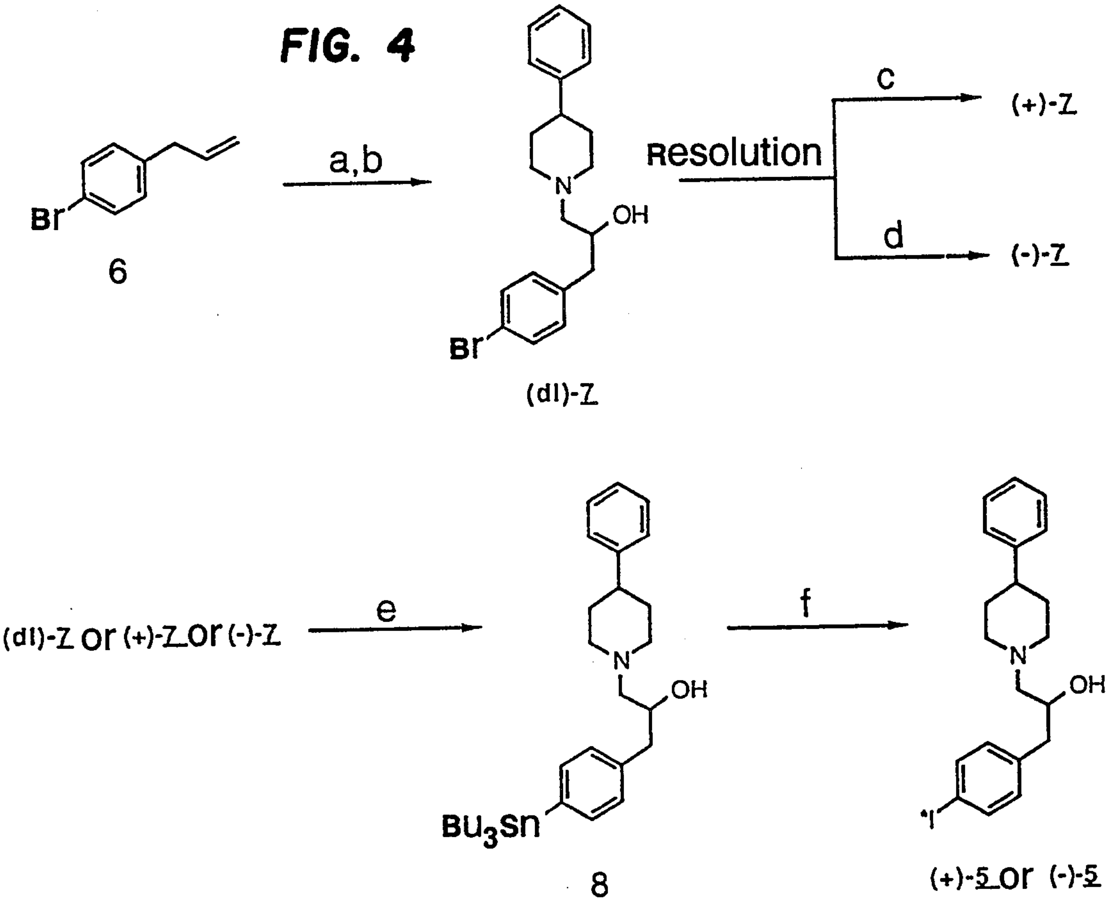
FIG. 4 shows a scheme for preparing compound 5.

The desired precursor 7 (HBrPP) was easily obtained from the previously described 6 (Jones et al 1970) in 53% yield (FIG. 4). The assignment of structure was based on the preferential attack of the secondary amine at the less hindered carbon of the epoxide. The methine proton at the C2 position of the propyl fragment appears as a multiplet at 3.92δ. The racemate 7 was successfully resolved by fractional crystallization of the diastereomeric tartarates to yield (+)-7 and (−)-7 in 97% ee and 92% ee respectively. Following halogen metal exchange and subsequent stannylation, 8 was obtained in yields as high as 64%. Extending the reaction time failed to substantially improve the yields. Racemic 5 was obtained from 8 in 36% by reaction of the latter with iodine in $CCl_4$. Racemic or enantiomerically enriched radioiodinated 5 was obtained from the corresponding precursor 8 by oxidative iodination with chloramine T in 73% radiochemical yield. The specific activity was between 100-200 Ci/mmol.

Results:

Tissue Distribution Studies

Biodistribution studies of (−)-[$^{125}$I]5 in rats show a significant accumulation of radioactivity within the brain and heart, two organs which receive significant cholinergic input (Table 1).

TABLE 1

Tissue distribution of (−)-4-[$^{125}$I]HIPP in the rat

| Tissue | % dose/g (range) 5 min. (n = 4) | 30 min. (n = 4) | 60 min. (n = 4) | 180 min. (n = 4) |
|---|---|---|---|---|
| Blood | 0.09 (0.06-1.33) | 0.03 (0.01-0.04) | 0.02 (0.01-0.03) | 0.01 (0.01-0.02) |
| Liver | 1.33 (0.91-1.70) | 2.28 (1.85-2.64) | 2.0 (1.65-2.82) | 2.43 (2.02-2.74) |
| Lung | 8.62 (7.57-9.94) | 4.80 (3.96-5.89) | 3.33 (2.75-4.20) | 2.52 (2.05-3.01) |
| Kidney | 2.89 (2.61-3.26) | 2.23 (1.66-2.59) | 1.85 (1.66-2.33) | 1.63 (1.38-1.94) |
| Muscle | 0.35 (0.20-0.52) | 0.19 (0.14-0.24) | 0.18 (0.16-0.21) | 0.16 (0.12-0.18) |
| Spleen | 0.87 (0.53-1.06) | 1.09 (0.89-1.28) | 1.40 (1.22-1.80) | 1.21 (1.18-1.24) |
| Heart | 1.32 (1.09-1.59) | 0.74 (0.59-0.98) | 0.72 (0.58-0.88) | 0.57 (0.50-0.65) |
| Brain | 1.03 (0.81-1.22) | 0.94 (0.67-1.20) | 0.98 (0.78-1.12) | 0.94 (0.88-1.00) |
| Brain: Blood | 12.3 | 31.3 | 55.5 | 69.7 |

TABLE 1-continued

Tissue distribution of (−)-4-[$^{125}$I]HIPP in the rat

| Tissue | 5 min. (n = 4) | 30 min. (n = 4) | 60 min. (n = 4) | 180 min. (n = 4) |
|---|---|---|---|---|
| | % dose/g (range) | | | |
| Ratio Heart: Blood Ratio | 16.4 | 26.8 | 40.3 | 42.5 |

At 5 minutes post injection, 1.94% of the injected dose was found in the brain. In addition, the concentration of radioactivity remained essentially stable within the brain for 3 hours. At 5 minutes post-injection, 1.2% of the injected dose was detected in the heart. In contrast to the brain, only 0.59% of the injected dose (a 50% reduction) was found in the heart after 3 hours. The level of radioactivity in the blood remained low throughout the study, suggesting that the radiolabel is fairly stable. Studies of (+)-[$^{125}$I]5 in the rat reveal a profile similar to that of (−)-[$^{125}$I]5 (Table 2).

TABLE 2

Tissue distribution of (+)-4-[$^{125}$I]HIPP in the rat

| Tissue | 5 min. (n = 4) | 30 min. (n = 4) | 60 min. (n = 4) | 180 min. (n = 4) |
|---|---|---|---|---|
| | % dose/g (range) | | | |
| Blood | 0.08 (0.07–0.09) | 0.04 (0.03–0.04) | 0.03 (0.02–0.03) | 0.03 (0.03–0.03) |
| Liver | 1.58 (1.02–1.99) | 2.55 (1.94–3.29) | 2.43 (2.11–3.09) | 2.38 (1.97–2.77) |
| Lung | 11.48 (7.47–15.37) | 5.59 (4.92–7.59) | 4.75 (4.10–5.54) | 3.74 (2.86–4.47) |
| Kidney | 2.84 (2.16–3.38) | 2.42 (1.95–2.70) | 2.30 (1.77–2.56) | 1.81 (1.51–2.10) |
| Muscle | 0.24 (0.13–0.38) | 0.25 (0.17–0.36) | 0.19 (0.56–0.22) | 0.24 (0.21–0.31) |
| Spleen | 0.71 (0.44–0.96) | 1.28 (1.0–1.51) | 1.23 (1.11–1.49) | 1.39 (1.17–1.57) |
| Heart | 1.80 (1.38–2.00) | 1.23 (1.10–1.41) | 1.12 (0.99–1.29) | 0.84 (0.76–0.91) |
| Brain | 1.20 (0.92–1.48) | 1.22 (0.96–1.73) | 1.23 (1.02–1.45) | 1.35 (1.02–1.62) |
| Brain: Blood Ratio | 15.2 | 32.4 | 44.3 | 44.8 |
| Heart: Blood Ratio | 22.7 | 32.7 | 40.2 | 28.2 |

At 5 minutes post-injection 2.27% of the injected dose was detected in the brain. The concentration remained essentially constant throughout the duration of the study. In the heart, 1.23% of the dose was found 5 minutes post-injection. Following a 32% decrease between 5 and 30 minutes, the level of radioactivity in the heart declined slowly over the duration of the study. The level of radioactivity in the blood remained low throughout the duration of the study. The similarity between the enantiomers of 5 contrasts with the biological profile of the recently reported 3. In the latter study, the brain retention of (+)-3 was significantly shorter than that of (−)-3 (Jung et al 1990).

Blocking Studies

The accumulation of either (+)-[$^{125}$I]5 or (−)-[$^{125}$I]5 in the rodent brain and heart was blocked by a co-administration with vesamicol (1.1 mol/kg), (+)-7 (1.3 μmol/kg) and (−)-7 (1.3 μmol/kg) respectively. All three compounds appeared to be equipotent in blocking the accumulation of [$^{125}$I]5 in vivo (Table 3*a,b*).

TABLE 3a

Inhibition of (−)-4-[$^{125}$I]HIPP accumulation in the rat

| Tissue | Group 1 (Control) (n = 3) | Group 2 (n = 3) | Group 3 (n = 3) | Group 4 (n = 3) |
|---|---|---|---|---|
| | % dose/g of tissue* (range) | | | |
| Blood | 0.02 (0.02–0.02) | 0.05 (0.04–0.06) | 0.04 (0.04–0.05) | 0.02 (0.02.0.03) |
| Liver | 2.68 (1.87–3.40) | 2.87 (2.87–2.97) | 1.90 (1.78–2.01) | 4.18 (3.85–4.54) |
| Lung | 3.63 (3.19–3.83) | 1.64 (0.55–2.77) | 1.04 (0.79–1.35) | 0.95 (0.65–1.17) |
| Kidney | 1.90 (1.32–2.23) | 0.46 (0.11–0.64) | 0.42 (0.36–0.56) | 0.35 0.31–0.39) |
| Muscle | 0.21 (0.19–0.26) | 0.07 (0.06–0.10) | 0.08 (0.06–0.10) | 0.06 (0.06–0.07) |
| Spleen | 1.42 (1.11–1.78) | 0.57 (0.41–0.85) | 0.57 (0.52–0.60) | 0.60 (0.56–0.65) |
| Heart | 0.79 (0.73–0.85) | 0.12 (0.08–0.17) | 0.13 (0.13–0.14) | 0.13 (0.11–0.14) |
| Brain | 0.93 (0.87–0.98) | 0.28 (0.20–0.38) | 0.29 (0.27–0.33) | 0.31 (0.29–0.34) |
| Brain: Blood Ratio | 42.7 | 5.6 | 7.1 | 12.7 |
| Heart: Blood Ratio | 36.5 | 2.5 | 3.0 | 4.9 |

TABLE 3b

Inhibition of (+)-4-[$^{125}$I]HIPP accumulation in the rat

| Tissue | Group 1 (Control) (n = 3) | Group 2 (n = 3) | Group 3 (n = 3) | Group 4 (n = 3) |
|---|---|---|---|---|
| | % dose/g of tissue* (range) | | | |
| Blood | 0.02 (0.02–0.02) | 0.06 (0.04–0.07) | 0.05 (0.04–0.06) | 0.04 (0.03–0.04) |
| Liver | 1.38 (1.09–1.73) | 1.13 (1.07–1.15) | 0.90 (0.68–1.05) | 2.23 (2.16–2.30) |
| Lung | 3.46 (2.91–3.93) | 1.29 (1.08–1.70) | 1.51 (0.81–2.14) | 1.11 (1.01–1.18) |
| Kidney | 1.63 (1.23–1.84) | 0.47 (0.43–0.48) | 0.54 (0.34–0.60) | 0.46 (0.42–0.51) |
| Muscle | 0.13 (0.12–0.14) | 0.08 (0.07–0.12) | 0.09 (0.06–0.11) | 0.08 (0.08–0.09) |
| Spleen | 1.10 (0.91–1.41) | 0.71 (0.64–0.83) | 0.57 (0.54–0.64) | 0.68 (0.61–0.76) |
| Heart | 0.60 (0.56–0.63) | 0.15 (0.13–0.16) | 0.16 (0.14–0.17) | 0.15 (0.15–0.15) |
| Brain | 0.76 (0.67–0.93) | 0.32 (0.26–0.37) | 0.32 (0.29–0.34) | 0.36 (0.34–0.37) |
| Brain: Blood Ratio | 28.7 | 3.9 | 4.5 | 9.7 |
| Heart: Blood Ratio | 39.8 | 1.8 | 2.0 | 3.8 |

*Animals in group 1 received an iv injection of (+)-4-[$^{125}$I]HIPP only. For groups 2, 3, and 4, the radiotracer was coadministered with the hydrochlorides of (+)-7 (0.53 mg/kg), (−)-7 (0.53 mg/kg) and vesamicol (0.31 mg/kg), respectively.

For (−)-[$^{125}$I]5, accumulation of radioactivity in the brain and heart was reduced by 70% and 84% respectively. For (+)-[$^{125}$I]5, reductions of 53%-58% and 74% -76% were observed in the brain and heart, respectively. In each case, the heart appeared to be slightly more sensitive to blocking than the brain.

To determine if vesamicol could displace bound [$^{125}$I]5 in vivo, a blocking dose of vesamicol was injected intravenously 30 minutes following the administration of (−)-[$^{125}$I]5. The same dose of vesamicol which blocks the accumulation of (−)-[$^{125}$I]5 when coadministered with the latter, fails to displace the bound radioactivity from the rodent brain or heart (data not shown).

Autoradiographic Studies

Figure 5:
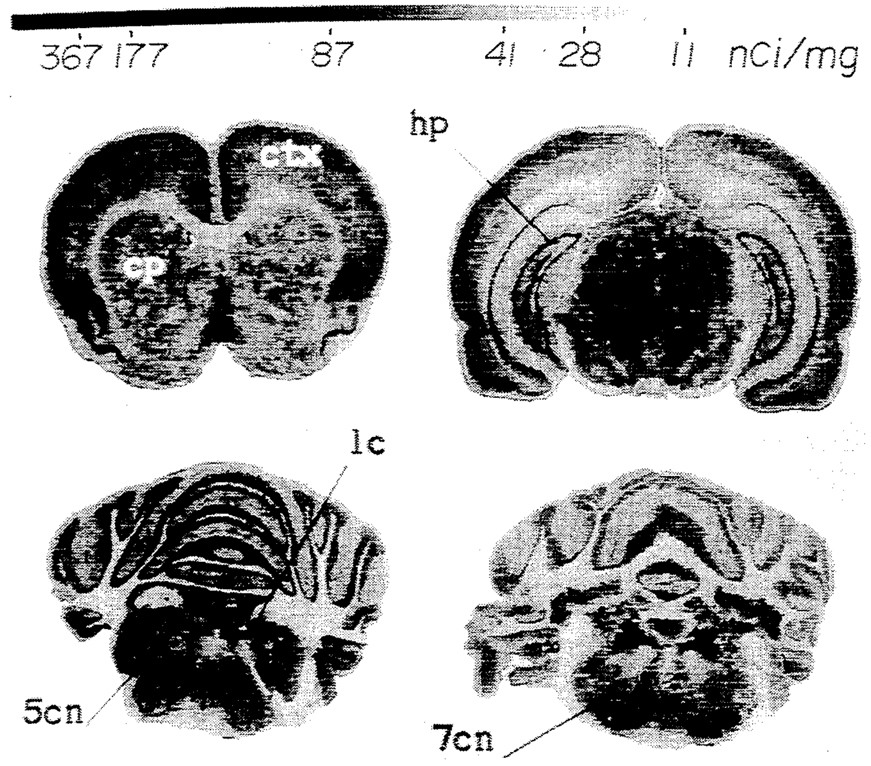
FIG. 5 is an autoradiograph of the rat brain showing the regional distribution of(−)-4[$^{125}$I]HIPP.

As revealed by Autoradiography, the regional distribution of (+)- and (−)-4[$^{125}$I]HIPP in the rodent brain was qualitatively similar. The highest levels of radioactivity were observed in the pineal gland and nuclei of the fifth (trigeminal) and seventh (facial) cranial nerves (FIG. 5). Moderate levels of radioactivity were observed within the frontal cortex and the caudate-putamen. Within the cerebellum the molecular layer showed a slightly higher concentration of radioactivity than the granular layer. The level of radioactivity in the white matter was relatively low. The pattern of distribution described for (+)- and (−)-4-[$^{125}$I]HIPP is qualitatively similar to that reported for [$^{3}$H] vesamicol in the rodent brain (Marien et al 1987, Altar et al 1988).

Brain Imaging Study

Figure 3:
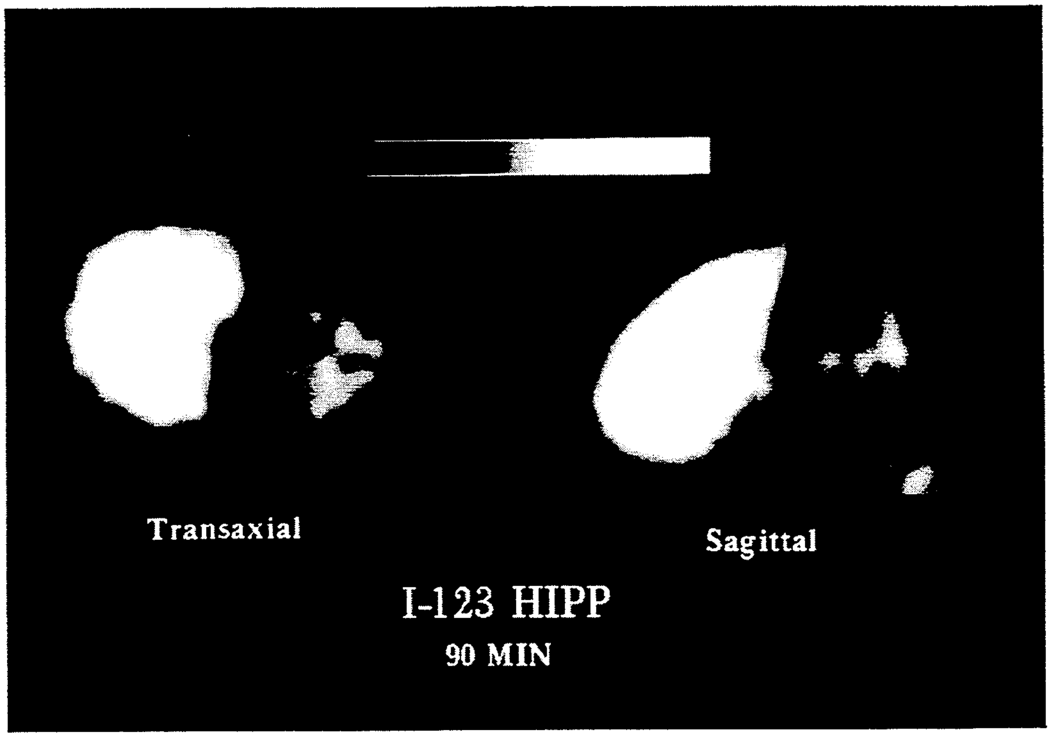
FIG. 3 is a SPECT image of (−)-4-[$^{123}$I]HIPP in the monkey brain.

Preliminary evaluation of (−)-4-[$^{123}$I]HIPP in the cynomolgus monkey showed significant accumulation of the radiotracer, estimated at 3% of the injected dose, within the brain (FIG. 3) In addition (−)-4-[$^{123}$I]HIPP exhibits prolonged retention in the monkey brain (t-$\frac{1}{2}$=9 hrs). Images of the primate obtained at 1$\frac{1}{2}$ and 18 hours post-injection were qualitatively similar. In both images, the brain clearly exhibits high levels of activity relative to the surrounding tissues. The Ventricles can also be easily visualized.

Figure 6:
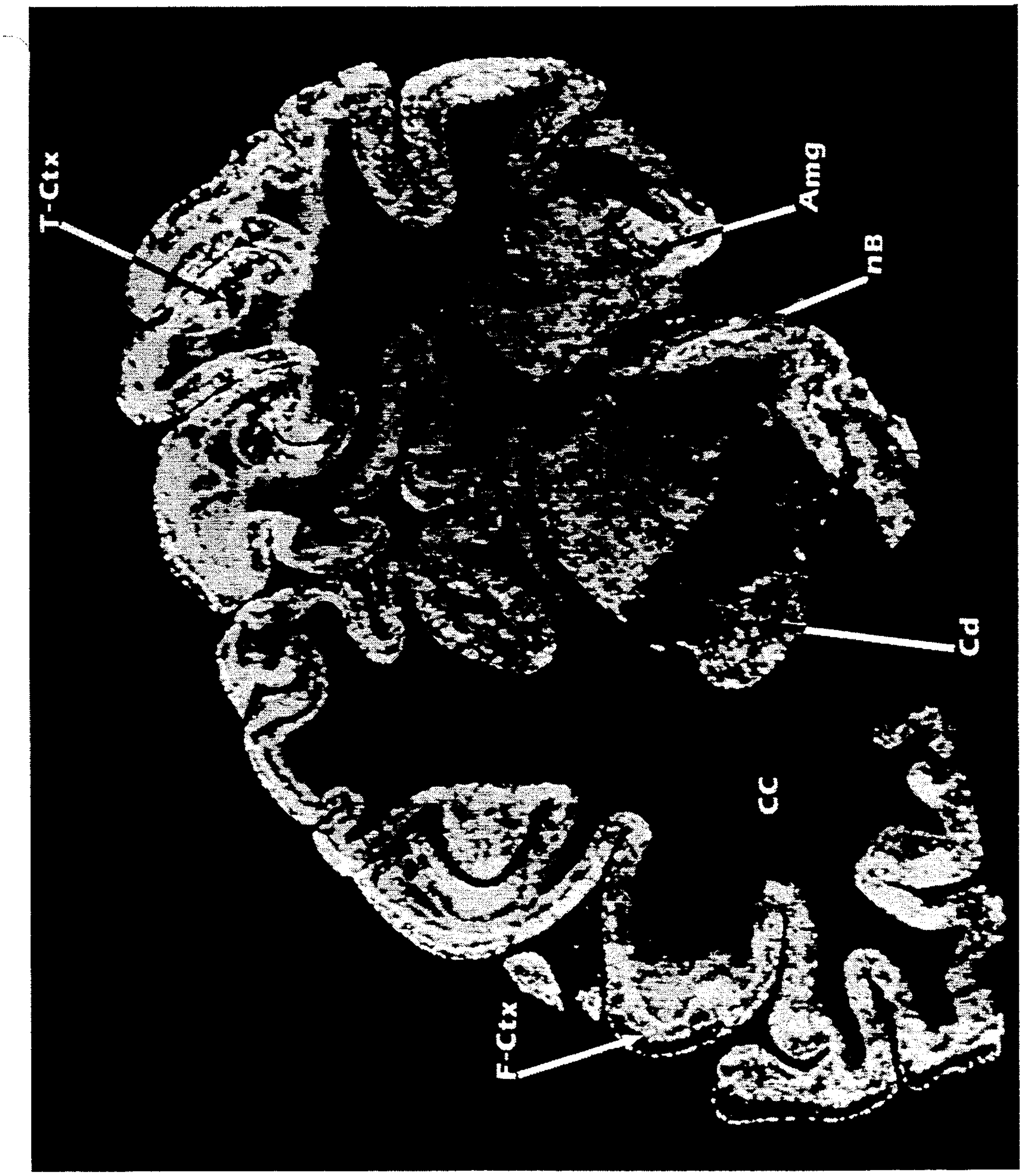
FIG. 6 shows the neuroanatomical distribution of the vesamicol receptor in the post-mortem human brain as revealed by in vitro autoradiography with (−)-4$^{125}$I]-HIPP.

FIG. 6 shows the neuroanatomical distribution of the vesamicol receptor in the post-mortem human brain (64-yr old normal male) as revealed by in vitro autoradiography with (−)-4-[$^{125}$I]HIPP. Note the high density in the cortex and nucleus basalis. High density: white, red. Medium density: blue, green. Low density: pink. Abbreviations: F-Ctx, frontal cortex; T-Ctx, temporal cortex; Amg, amygdala; cc, corpus callosum; Cd, caudate; GP, globus pallidus; nB, nucleus basalis.

Discussion

Earlier studies of vesamicol analogs provided a number of clues relating to potency and molecular recognition. Whereas 4 was found to be two hundred and fifty times less potent than the parent vesamicol, the former was nonetheless a vesamicol analog (Rogers et al 1989). The latter observation suggested that 4 represents the minimum stereoelectronic requirements for recognition at the vesamicol receptor, and may therefore be used as a template for structural modification. In addition to their increased potency relative to the parent vesamicol, the "benzo" analogs dissociate from the receptor at a significantly slower rate (Rogers et al 1990). A stereochemically simple analog (such as 5) which contains both the basic elements defined by 4 and a lipophilic group superimposable on the "benzo" portion of 1 would be a potent ligand for the vesamicol receptor. In addition, 5 would provide a simple radiotracer for mapping central cholinergic pathways.

Compound 5 was successfully synthesized and evaluated in the rodent and monkey. The results of these studies indicate: 1) that the in vivo binding of radiolabelled 5 can be blocked by vesamicol (and its analogs) and 2) that the regional distribution of this radiotracer in the rodent brain is similar to that described for [$^{3}$H] vesamicol. Based on these observations, it was concluded that the original hypothesis was correct, and 5 is therefore a potent ligand for the vesamicol receptor.

In both the rodent and monkey, radiolabelled 5 achieved significant concentrations in the brain. Furthermore, this radiotracer exhibits prolonged brain retention comparable to that reported for the benzovesamicol analog (−)-[$^{125}$I]3. In the monkey brain, the half-life of (−)-4-[$^{123}$I]HIPP is estimated to be 9 hours. However, such a retention may be attributed to a number of events, including: 1) slow dissociation of ligand from receptor, 2) rapid recapture of disassociated ligand by available unoccupied receptors and 3) covalent binding of ligand to receptor. Preliminary evaluation of rodent brain extracts suggest that the ligand is not covalently bound to the receptor. However, the observation that (dl)-vesamicol can not readily displace (−)-[$^{125}$I]5 in vivo is consistent with a slowly dissociating ligand. The slow dissociation of some vesamicol analogs from the vesamicol receptor may be attributed to a poorly understood phenomenon in which the receptor becomes refractory to competing ligands following initial ligand binding (Rogers and Parsons, 1990).

Studies of radiolabeled 3 in the rodent indicate that the brain retention of the levorotary isomer (−)-[$^{125}$I]3 is much longer than that of the corresponding antipode. The behavior of these two enantiomers of 3 contrasts with that of (+)- and (−)-4-[$^{125}$I]HIPP. The latter enantiomers appear to exhibit a comparable retention in the brain. Given the close structural similarity between 5 and 3, it may be tempting to suggest that the enantioselectivity observed for 3 is attributable to constraints imposed upon this structure by the cyclohexyl ring. The corollary would be that 5, given its inherent flexibility, can easily accommodate the receptor. However, the relative positions of the halogens in 5 and 3 introduces some uncertainty into such a comparison.

Finally, preliminary evaluation of the radiolabeled 1,3-disubstituted propan-2-ol 5 suggests that the latter binds to the vesamicol receptor in vivo. Given its high accumulation and prolonged retention in the primate brain, 5 may be potentially useful for mapping central cholinergic innervation in vivo.

Experimental

General Synthetic intermediates were purchased from Aldrich Inc (Milwaukee Wis.) and were used as received. Solvents were distilled immediately prior to use. Commercially available reagents were used without subsequent purification. Tissue Tek OCT compound was obtained from Miles, Inc. Elkhart, IN and rats were purchased from Sasco Inc., Omaha, Nebr.

All air sensitive reactions were carried out under nitrogen. Standard handling techniques were determined on a MeI-Temp melting point apparatus and are uncorrected. The specific rotation was determined on an automatic polarimeter (Autopol III, Rudolph Research, Flanders, N.J.) $^{1}$H NMR spectra were recorded on an IBM Brucker spectrometer at 200 MHz. NMR spectra are referenced to the deuterium lock frequency of the spectrometer. With this condition, the chemical shifts (in ppm) of residual solvent in the $^{1}$H NMR were found to be respectively $CHCl_3$, 7.26, DMSO, 2.56, HOD 4.81. The following abbreviations are used to describe peak patterns when appropriate: b=broad, s=singlet, d=doublet, t=triplet, q=quartet, m=multiplet. Both low and high resolution MS were performed on an AEI MS-30 instrument. Elemental analysis were performed by Atlantic Microlab, Inc., Norcross, Ga.

Column chromatography was performed using "Baker Analyzed" silica gel (60–200 mesh). Preparative chromatography was performed on a Harrison Research Chromatotron using Merck 60 PF 254 silica gel. Analytical TLC was performed on Analtech glass TLC plates coated with silica gel GHLF and were visualized with UV light and/or methanolic iodine.

2-Hydroxyl-1-(4-phenylpiperidino)-3-(-4-bromophenyl)propane, (Compound 7).

Compound 6 was prepared in 80% yield as previously described. m-Chloroperoxybenzoic acid (6.9 g of 50–55% purity) was added portionwise to a cold solution of 4.0 g (20 mmol) of 6 in 100 ml of methylene chloride. Following the addition, the reaction mixture was maintained at 4° C. for an additional 60 minutes and allowed to warm up to room temperature. Stirring was continued overnight. After 23 hours, the mixture was treated with $CCl_4$ (100 ml) and filtered to remove the precipitated m-chlorobenzoic acid. The flitrate was washed consecutively with 5% aq. $NaHSO_3$ (100 ml) and satd $NaHCO_3$ (2×100 ml), dried over anhydrous $Na_2SO_4$, and concentrated in vacuo to give the epoxide as a colorless liquid (3.6 g). The latter was used without further purification.

A solution of the epoxide and 2.42 g (15 mmol) of 4-phenylpiperidine in absolute ethanol (60 ml) was refluxed for 20 hours and concentrated in vacuo to a residue. The latter was dissolved in $CH_2Cl_2$ (70 ml) and the resulting solution was washed with $H_2O$ (50 ml), dried over anhydrous $Na_2SO_4$ and concentrated to a syrup. The crude product was purified by preparative HPLC on silica gel (isopropyl alcohol, 20: hexanes, 79: $Et_3N$, 1) to yield a white solid. The product was recrystallized from hexanes to provide 2.70 g (48%) of crystalline Z. $^1H$ NMR ($CDCl_3$) δ1.65 (m, 4H), 2.01 (t,1H), 2.32–2.93 (m, 7H), 3.08 (d, 1H), 3.78 (br s, 1H), 3.92 (m, 1H), 7.13–7.36 (m, 7H), 7.46 (d, 2H). Yields ranging from 40 to 53% were subsequently obtained on larger runs. A solution of the free base 7 in methanol was cooled in an ice bath and HCl gas was bubbled through this solution for 10 minutes. The resulting solution was concentrated to a residue which was recrystallized from isopropyl alcohol to yield the hydrochloride of 7 as a white solid; mp 194°–198° C. Anal. ($C_{20}H_{24}BrNO.HCl$) calcd: C, 58.48; H, 6.13; N, 3.41. Found: C, 58.39; H, 6.12; N, 3.44.

Resolution of (dl)-7.

Compound 7 was resolved according to a procedure described earlier for vesamicol. Di-p-toluoyl-L-tartaric acid monohydrate (4.72 g, 11.67 mmol) was added portionwise, at room temperature, to a stirring solution of (dl)-7 (4.0 g, 10.7 mmol) in 50 ml of acetone. Following the addition, stirring was continued at room temperature for 12 h. At this time the resulting crystals were collected by filtration, dried and weighed to provide 4.8 g. of the crude product. The latter was dissolved in 220 ml of boiling acetonitrile and cooled to 4° C. After 12 hours, the product was collected by filtration and dried to yield 3.3 g of tartrate; $[\alpha]_D=-48.68$ (c=0.025, MeOH). Subsequent recrystallization of this product from 190 ml of boiling acetonitrile provided 2.6 g (63%) of the (−)-tartrate of 7; mp 184.9° C. The free base (−)-7 was obtained by treatment of the tartrate with satd $NaHCO_3$ and subsequent extraction into $CH_2Cl_2$ (3×30 ml). The enantiomeric purity of (−)-7 was estimated by HPLC using a Chiralcel OD column (10% isopropyl alcohol-hexanes; flow rate: 1 ml/min; retention time: 7.2 min.) to be 94%. All the mother liquors from above were combined and concentrated in vacuo to a residue. The latter was treated with $^1M$ NaOH (70 ml) and resulting mixture was extracted with EtOAc (250 ml). The organic extract was dried over $Na_2SO_4$ and subsequently concentrated to provide 2.34 g of free base enriched in (+)-7. The latter sample was dissolved in acetone (25 ml) and treated dropwise with a solution of 2.76 g (7.14 mmol) of (+)-di-p-toluolyltartaric acid monohydrate in an equal volume of acetone. After stirring for 16 hours, the crystals were collected, dried and recrystallized from boiling acetonitrile (2×200 ml) to yield 1.85 g (40%) of (+)-7 tartrate; mp 186° C., $[\alpha]_D=+49.5°$ (c=0.023, MeOH). The enantiomeric purity of the free base (+)-7 was estimated as outlined above to be 98.6% (retention time: 12.3 min.).

2-Hydroxy-1-(4-phenylpiperidinyl)-3-[4-(tri-n-butyl)-stannylphenyl]propane. (Compound 8).

A solution containing 1.0 g (2.7 mmol) of 7 in dry THF (40 ml) was cooled, under $N_2$, in a Dry Ice-acetone bath. To this solution was added dropwise, 2.5 ml (6.2 mmol) of n-BuLi in hexanes. Following the addition, the Dry Ice-acetone bath was maintained for 100 minutes at which time a solution of 1.9 g (5.9 mmol) of $n-Bu_3SnCl$ in 10 ml of THF was added dropwise over 10 minutes. The Dry. Ice-acetone bath was then removed and the reaction mixture was allowed to warm up to room temperature. After 14 hours, the reaction mixture was treated with methanol and the resulting solution was concentrated in vacuo to a residue. The latter was purified by preparative HPLC on a silica gel column (isopropyl alcohol, 10: hexanes, 89: triethylamine, 1) to yield the product 8 as a colorless oil (0.5 g, 32%). Twenty-five percent of the starting material was also recovered. Similar runs using (+)-7 and (−)-7 provided the corresponding (+)-8 and (−)-8 in yields of 55% and 65%, respectively. $^1H$ NMR ($CDCl_3$) δ0.60–1.89 (m, 18H), 2.02 (t, 1H) 2,38–2.90 (m, 7H), 3.10 (d, 1H), 3.97 (m, 1H), 7.17–7.57 (m, 9H). CIMS (70 eV) m/e (intensity) 585.1 ($M^++2$, 79), 587.1 ($M^++2$, 100).

(dl)-2-Hydroxy-3-(4-iodophenyl)-1-(4-phenylpiperidyl)-propane, (Compound 5).

A solution of 0.85 g (0.09 mmol) of 8 in $CCl_4$ (5 ml) was cooled in an ice bath. To this solution was added dropwise a solution of iodine (0.64 g; 0.25 mmol) in $CCl_4$. Following the addition, the ice bath was removed and the reaction mixture was stirred, with exclusion of light, overnight. The solvent was then removed in vacuo and the residue was dissolved in 60 ml of $CH_2Cl_2$. The latter solution was washed consecutively with 5% aq. $NaHCO_3$ (50 ml), 10% aq. $NaHCO_3$ (100 ml) and brine (50 ml), dried over $Na_2SO_4$ and finally concentrated to a residue. The crude product was purified by preparative TLC on 20×20 silica gel plates (acetone, 1: hexanes, 2.5; 0.1% $Et_3N$) to yield 130 mg (36%) of the pale yellow semisolid 5. $^1H$ NMR ($CDCl_3$) δ1.37–3.28 (m, 14H), 3.91 (m, 1H), 7.01 (d, 2H), 7.27 (m, 5H), 7.62 (d, 2H). The latter was converted to the corresponding hydrochloride (as described for 7 above) and recrystallized from isopropyl alcohol-ether to yield an off-white solid; mp 199°–201° C. Anal. ($C_{20}H_{24}INO.HCl$) Calcd: C, 52.48; H, 5.50; N, 3.06. Found: C, 52.38; H, 5.50; N, 3.14.

Radiolabelling

To a 10×75 mm borosilicate vial, the following were added in the stated order: 50 μl of a 10 mM solution of (+)- or (−)-8 in methanol, 50 μl of EtOH, 50 μl of HOAc, $\mu l$ (8.65 mCi) of $Na^{125}I$ in aq NaOH (pH 10) and chloramine T (2 mg). The vial was vortexed for 15 seconds, and allowed to stand at room temperature for 15 minutes. At this time, the reaction was quenched with 100 $\mu l$ of 5% of aq. $NaHSO_3$ and vortexed for 15 seconds. The resulting mixture was treated with solid $NaHCO_3$ (100 mg) and extracted with $CH_2Cl_2$ (3×0.5 ml). The combined organic extracts were dried over anhydrous $Na_2SO_4$ and concentrated to a residue under a stream of $N_2$. The residue was dissolved 50% methanol—$CH_2Cl$(100 $\mu l$) and purified by reverse phase HPLC (MeOH-5 mM phosphate buffer, pH 7.8; flow rate 4 ml/min.) on a 10-mm $C_{18}$ reverse phase column. The retention time was 16.72 minutes. The eluent was treated with 50 $\mu l$ of aqueous oxalic acid (5 mg/50 $\mu l$) and concentrated to yield 6.35 mCi (73%) of the product which was determined to be approx. 99% radiochemically pure. The $^{123}I$-labelled compound was prepared under similar conditions, and with similar yields.

The pure radioiodinated enantiomers, (+)-5 or (−)-5 could also be obtained from the corresponding racemate, (dl)-5, by HPLC on a Chiralcel OD column (10% isopropyl alcohol/hexanes, 0.2% $Et_2NH$; 1 ml/min.). The retention times for (−)-5 and (+)-5 were 7.74 and 18.05 min., respectively. The specific activity determined from a Beer-Lambert standard curve, was between 100–200 Ci/mmol. Finally the radiolabelled material was dissolved in 50% aqueous ethanol and used for biological studies.

The compounds of the invention may be labeled by any of several techniques known in the art. Among the radioisotopes used, gamma-emitters, X-ray emitters and fluorescence emitters are suitable, including Iodine-131, Iodine-123, Iodine-125, Iodine-126, Iodine-133, Bromine-77, Indium-11, Indium-113m, Gallium-67, Gallium-68, Ruthenium-95, Ruthenium-97, Ruthenium-103, Ruthenium-105, Mercury-107, Mercury-203, Rhenium-99m, Rhenium-101, Rhenium-105, Tellurium-121m, Tellurium-122m, Tellurium-125m, Thulium-165, Thulium-167, Thulium-168, Technetium-99m and Fluorine-18. Technetium is a preferred isotope and is preferably provided in a kit form with the compound and a Technetium generator.

Biological

Tissue Distribution Experiments

Four groups of male Wistar rats (with four animals per group) weighing 200–350 g were used in these experiments. Each animal received, while under ether anesthesia, an intravenous injection of the radiotracer (10–20 $\mu$Ci) dissolved in 0.1 ml of 50% aqueous ethanol. At 5, 30, and 60 and 180 min. post-injection, blood was collected from the anesthetized animals by cardiac puncture, and the animal was immediately sacrificed by cardiectomy. The organs and tissues of interest were harvested, transferred to preweighed tubes and counted in a Beckman gamma counter. The tubes were subsequently reweighed to give the weight of the corresponding tissues. Preweighed tubes containing $^1$-ml samples of a 1:100 dilution of the injection dose were also counted and used as reference for calculating the tissue accumulation of radioactivity. The accumulation of radiotracer was expressed as a percentage of injected dose per gram of tissue.

Blocking Experiments

Four groups of male Wistar rats (n=3) were used in these experiments. All animals received an iv dose of 8–10 $\mu$Ci of the radiotracer in 0.1 ml of 50% aq. ethanol.

Additionally, in groups 2, 3 and 4, the radiotracer was coadministered with (+)-HBrPP.HCl(1.3 $\mu$mol/kg), (−)-HBrPP.HCl(1.3 $\mu$mol/kg) and (dl)-vesamicol hydrochloride (1.1 $\mu$mol/kg), respectively. At 60 min. post-injection, blood was collected by cardiac puncture and the animals sacrificed as described above. The data was analyzed as outlined above.

Ligand Displacement Studies

Two groups of male Wistar rats (n=3) were used in this study. Each animal initially received, while under anesthesia, an iv dose of (−)-5, (9.5 $\mu$Ci) in 0.1 ml of 50% aqueous ethanol. After 30 min. the control group received an iv dose of 50% aqueous ethanol (0.1 ml) while the second group received an iv dose of (dl)-vesamicol hydrochloride (1.1 $\mu$mol/kg) in 0.1 ml of 50% aqueous ethanol. All animals were sacrificed, as described above, at one hour following radiotracer injection. Data was analyzed as described above.

Ex vivo Autoradiograpic Studies

Four male Wistar rats weighing 300–330 g. were anesthetized with diethyl ether. While under anesthesia two animals each received an intravenous dose of 300 $\mu$Ci of (−)-4-[$^{125}$I]HIPP in 200 ml of 50% aqueous ethanol. The second pair of animals received an iv dose of (+)-4-[$^{125}$I]HIPP (170 $\mu$Ci) in the same solvent. The animals were sacrificed by decapitation three hours following radiotracer administration. The brains were harvested, embedded in Tissue Tek OCT embedding medium and frozen to −38° C. Twenty-micron thick brain sections were obtained at −15° C. using a Reicheft HistoSTAT cryostat microtome. The sections were dried and opposed to Kodak NMC film for autoradiography accompanied by external standards ($^{125}$I-labelled microscales from Amersham). Images were subsequently digitized based on the linear scale obtained from these standards.

Imaging Studies

These studies were conducted with a Picker 3-head PRISM camera equipped with a high-resolution fan beam collimator. A 5-Kg male cynomolgus monkey, anesthetized with halothane, received an intravenous dose of 12 mCi of (−)-4-[$^{123}$I]HIPP ((−)-[$^{123}$I]5) in 1 ml of 50% ethanol-isotonic saline. Data acquisition which commenced simultaneously, in the "step and shoot" mode, was divided into one 5minute segment, six 10-minute segments and a final 20-minute segment. At 18 hours post-injection, data was acquired under similar conditions for both the head and the heart, over a 20 minute period. For cardiac imaging, the camera was equipped with a medium-energy-parallel-hole collimator. The data was subsequently processed to obtain both a time-activity curve and images in the transaxial and sagittal planes. To obtain an estimate of the fractional accumulation of (−)-4-$^{123}$I]HIPP in the monkey brain, a phantom filled consecutively with varying concentrations of aqueous $Na^{125}I$ was counted with the gamma camera to generate a standard curve.

Compound 9 was synthesized in the same manner as 7 (FIG. 4). Compound 10 was also synthesized in a similar fashion from the commercially available 4-bomostyrene. Compounds 12 and 13 and their radiolabelled counterparts were synthesized by the same procedures already elaborated for 5.

Biodistribution Studies with [$^{125}$I]12 (Compound 12)

In the rat brain, the initial accumulation of both (+)-[$^{125}$I]12 and (−)-[$^{125}$I]12 was 2.08 and 1.86% of the injected dose, respectively (Table 4 and 5). At 1 and 3 hours, post-injection, the concentration of (−)-[$^{125}$I]12 decreased by 43% and 74%, respectively. In contrast, the concentration of (+)-[$^{125}$I]12 at the same time had only decreased by 20% and 54%, respectively. The accumulation of both enantiomers of [$^{125}$I]12 was inhibited by co-administration with (dl)-vesamicol, suggesting that these compounds bind to the vesamicol receptor (Table 6 and 7).

Biodistribution Studies with [$^{125}$I]13 (Compound 13)

In contrast to radiolabelled 12, (+)-[$^{125}$I]13 achieved significantly higher initial brain concentrations than (−)-[$^{125}$I]13 (2.75 vs. 1.69% of the injected dose). In addition the efflux (+)-[$^{125}$I]13 from the brain was much slower than that of the levorotary enantiomer (see Table 8 and 9). At 3 hours post-injection, the levels of (+)[$^{123}$I]13 had decreased by 35%. On the other hand, the levels of (−)-[$^{125}$I]13 had decreased by 85%. Furthermore, the accumulation of both (+)-[$^{125}$I]13 and (−)-[$^{125}$I]13 was decreased by coadministration of (dl)-vesamicol (Table 10), thereby confirming that 13 binds to the vesamicol receptor.

(dl)-3-(3-Bromophenyl)-2-hydroxy-1[1-(4-phenyl)-piperidyl]propane, 9 (Compound 9).

Compound 9 was synthesized, by the same procedure elaborated for 7 in an overall yield of 30% from 1,3-dibromobenzene. The free base of 9 was converted to its corresponding hydrochloride as described for 7; mp 161°-163° C. $^1$H NMR (DMSO-d$_6$) δ1.90 (m,2H), 2.16 (m,2H), 2.78 (m,2H), 3.10(m,4H), 3.38(br s, $^1$H), 3.63(m,2H), 4.35(br s, 1H), 5.72 (m, 1H), 7.37 (m,9H), 10.30(br s, 1H). Anal. calcd. for $C_{20}H_{24}BrNO.HCl$: C, 58.48; H. 6.13; N,3.41 Found: C, 60.27; H, 6.41; N, 3.50.

(+)-2-Hydroxy-1-(4-phenylpiperidinyl3-(3-tributyl-stannylphenyl)propane

Following the procedure given for 8, n-BuLi (2.5 M, 5.1 mL, 12.9 mmol) was added to a solution of (+)-3-(3-bromophenyl)-2-hydroxyl-1[1-(4-phenylpiperidinyl)]-propane (2.4 g, 6.4 mmol) in THF (50 mL) at −78° C. After 2 hr, n-Bu$_3$SnCl (1.7 ml, 6.4 mmol) was added and the mixture stirred at room temperature for 16 hr. Workup afforded 1.7 g (46.1%) of a yellow oil. $^1$H NMR (CDCl$_3$) δ5 0.95 (t,9H, J=7.2 HZ), 1.11 (m,6H), 1.46 (m,6H), 1.55 (m,6H), 1.83 (m,4H), 2.03 (m,1H), 2.41 (m,4H), 2.73 (m,1H), 2.93 (m,2H), 3.12 (d, 1H,J=11.02 Hz), 3.78 (b-s, 1H), 4.01 (m,1H), 7.30 (m,9H), $^{13}$C NMR (CDCl$_3$) ppm 9.69, 13.82, 27.49, 29.24, 33.57, 33.93, 41.79, 42.63, 52.79, 56.34, 64.02, 67.68, 126.28, 126.89, 127.96, 128.52, 129.19, 134.51, 137.59, 137.73, 141.96, 146.25. CIMS (NH3)m/e (intensity) 585.1 ((M+2H)+, 34.8), 587.1 ((M+2H)+, 42.0).

(+)-2-Hydroxyl-3-(3-iodophenyl)-1-[1-(4-phenyl-piperidinyl)]propane, 12 (Compound 12)

A solution of (+)-2-hydroxyl-l-[1-(4-phenyl-piperidinyl]-3-(3-tributylstannylphenyl)propane (1.73 g, 2.96 mmol) in CCl$_4$ (2 mL) was added to a solution of iodine (0.91 g, 3.60 mmol) in CCl$_4$(40 mL). The flask was covered with foil to exclude light and the solution stirred at room temperature for 16 hour. The mixture was poured into sat. $Na_2CO_3$:5% $NaHSO_3$ (1:1 v:v, 100 mL) and extracted with CCl$_4$ (3×50 mL). The combined organic layers were dried over $Na_2SO_4$, filtered and concentrated under reduced pressure. The residue was separated by HPLC eluting with hexane:i-PrOH-:Et$_3$N (90:10:1). The combined eluents were concentrated under reduced pressure to give 0.61g (49.2%) of a pale yellow oil. The hydrochloride was prepared by treating an ethanolic solution of the amine with HCl (g) and precipitating out the salt with Et$_2$ O to give pale yellow crystals (mp 178°-80° C.). $^1$H NMR (d$_6$-DMSO) δ1.91 (m,2H), 2.15 (m,2H), 2 .75 (m,2H), 3.11 (m,3H), 3.42 (s,2H), 3.63 (m,2H), 4.34 (b-s,1H), 5.71 (m,lH), 7.12 (t,1H,J=7.7 Hz), 7.30 (m,6H), 7.60 (d,1H,J=7.9 Hz), 7.70 (s,1H), 10.33 (b-s,1H). $^{13}$C NMR (d$_6$-DMSO) ppm 29.88, 38.80, 40.58, 52.35, 53.71, 62.12, 65.63, 94.94, 126.73, 128.71,129.23, 130.48, 135.12, 138.15, 140.94, 144.52, Anal. Calcd for $C_{20}H_{25}ClINO$ (Hydrochloride): C, 52.47; H, 5.50; N 3.06 Found: C, 52.49; H, 5.48; N, 3.02.

(dl)-1-(4-bromophenyl)-2-(4-phenylpiperidinyl)ethanol, 10 (Compound 10)

Compound was obtained from the epoxidation of 4-bromostyrene and subsequent reaction of the epoxide with 4-phenylpiperidine in ethanol. The product was purified by HPLC (20% isopropyl alcohol-hexanes, trace Et$_3$N;silica gel) to yield a white solid. yield, 48%. $^1$H NMR (CDCl$_3$) δ1.86 (m, 4H); 2.17 (t, 1H), 2.37-2.55 (m, 4H), 2.93 (d, 1H), 3.26 (d, 1H), 4.26 (bR s, 1H), 4.72 (dd, 1H), 7.22-7.36 (m, 7H), 7.48 (d, 2H). The hydrochloride was recrystallized from isopropyl alcohol, mp 233°-236° C. Anal. calcd. for $C_{19}H_{22}BrNO.HCl$: C, 57.66; H, 5.85; N, 3.54. Found: C, 56.47; H, 6.04; N, 3.43.

1-(4-Iodophenyl)-2-(4-phenylpiperidinyl)ethanol (Compound 13)

1-[4-(Tri-n-butyl)stannylphenyl]-2-(4-phenyl-piperidinyl)ethanol was obtained as a pale yellow solid in 73% yield from 10, following the procedure elaborated for 8 (See Fig. 4). $^1$H NMR (CDCl$_3$) δ0.91 (t,9H), 1.02-1.91 (m,22H), 2.17 (t,1H), 2.45-2.61 (m,4H), 2.97 (d,1H, J=12.0 Hz), 3.32 (d, $^1$H, J=11 Hz), 4.19 (br s, 1H), 4.76 (m, 1H), 7.19-7.59 (m, 9H). CIMS (NH$_3$) m/e (intensity) 580.7 [M+2H+, 30.2], 572.7 (M+2H+, 42.0).

This intermediate converted to 13 in 26% yield following the procedure elaborated for 12. The free base was converted to the corresponding hydrochloride by the usual procedure; mp 241°-244.5° C. $^1$H NMR (DMSO-d$_6$) δ1.80-2.30 (m, 4H), 2.83 (m, 1H), 3.24 (m, 4H), 3.75 (m, 2H), 5.26 (d, 1H), 7.26-7.39 (m, 7H), 7.77 (d, 2H, J=8.2 Hz), 10.55 (br s, 1H).

TABLE 4

Tissue Distribution of (+)-[$^{125}$I]12 in the Rat (injected dose: 11 uCi).

| TISSUE | % dose/g of tissue (range) TIMEPOINT 5 MIN (n = 3) | 60 MIN (n = 3) | 180 MIN (n = 3) |
|---|---|---|---|
| blood | 0.08 | 0.09 | 0.08 |
| | 0.07 to 0.09 | 0.08 to 0.09 | 0.07-0.09 |
| liver | 1.17 | 0.89 | 0.51 |
| | 1.05 to 1.35 | 0.72 to 1.01 | 0.46-0.62 |
| lung | 7.34 | 1.42 | 0.61 |
| | 5.77 to 8.34 | 1.31 to 1.61 | 0.57-0.68 |
| kidney | 2.55 | 1.28 | 0.75 |
| | 2.23-2.69 | 1.12 to 1.32 | 0.72-0.80 |
| muscle | 0.27 | 0.16 | 0.12 |
| | 0.18 to 0.38 | 0.14 to 0.23 | 0.10-0.15 |
| spleen | 0.50 | 1.12 | 0.66 |
| | 0.46 to 0.54 | 1.10 to 1.14 | 0.63-0.69 |
| heart | 1.30 | 0.38 | 0.16 |
| | 1.15 to 1.41 | 0.35 to 0.42 | 0.15-0.17 |
| brain | 1.03 | 0.82 | 0.56 |
| | 0.95 to 1.17 | 0.78 to 0.89 | 0.50-0.62 |
| Brain: Blood Ratio | 13.1 | 9.2 | 7.2 |
| Heart: Blood Ratio | 16.4 | 4.2 | 2.1 |

TABLE 5

Tissue Distribution of (−)-[$^{125}$I]12 in the Rat (injected dose: 11 uCi).

| TISSUE | % dose/g of tissue (range) TIMEPOINT 5 MIN (n = 3) | 60 MIN (n = 3) | 180 MIN (n = 3) |
|---|---|---|---|
| blood | 0.11 | 0.11 | 0.11 |
| | 0.10 to 0.12 | 0.10 to 0.12 | 0.10–0.12 |
| liver | 1.41 | 1.04 | 0.79 |
| | 1.10 to 1.66 | 0.94 to 1.16 | 0.64–0.93 |
| lung | 8.94 | 1.04 | 0.46 |
| | 6.19 to 10.71 | 0.94 to 1.20 | 0.37–0.53 |
| kidney | 2.46 | 1.00 | 0.59 |
| | 1.79–2.85 | 0.90 to 1.04 | 0.46–0.66 |
| muscle | 0.36 | 0.14 | 0.08 |
| | 0.26 to 0.49 | 0.12 to 0.18 | 0.07–0.10 |
| spleen | 0.66 | 0.95 | 0.44 |
| | 0.47 to 0.77 | 0.88 to 1.03 | 0.44–0.44 |
| heart | 1.26 | 0.21 | 0.10 |
| | 1.13 to 1.43 | 0.17 to 0.22 | 0.09–0.10 |
| brain | 0.98 | 0.56 | 0.27 |
| | 0.78 to 1.13 | 0.51 to 0.62 | 0.23–0.32 |
| Brain: Blood Ratio | 9.0 | 5.1 | 2.6 |
| Heart: Blood Ratio | 11.4 | 1.9 | 0.9 |

TABLE 6

Inhibition of (+)-[$^{125}$I]12 accumulation in the rat.

| TISSUE | % dose/g of tissue (range) GROUP I (n = 3) | GROUP II (n = 3) | GROUP III (n = 3) |
|---|---|---|---|
| blood | 0.09 | 0.13 | 0.12 |
| | 0.08 to 0.10 | 0.12 to 0.13 | 0.11 to 0.14 |
| liver | 0.86 | 0.71 | 0.87 |
| | 0.81 to 0.97 | 0.67 to 0.75 | 0.83 to 0.96 |
| lung | 1.52 | 0.92 | 0.71 |
| | 1.26 to 1.84 | 0.62 to 1.29 | 0.60 to 0.86 |
| kidney | 1.48 | 0.62 | 0.55 |
| | 1.36 to 1.55 | 0.57 to 0.67 | 0.39 to 0.66 |
| muscle | 0.17 | 0.11 | 0.12 |
| | 0.12 to 0.23 | 0.10 to 0.13 | 0.09 to 0.14 |
| spleen | 1.14 | 0.50 | 0.48 |
| | 1.04 to 1.33 | 0.47 to 0.53 | 0.34 to 0.61 |
| heart | 0.36 | 0.15 | 0.13 |
| | 0.33 to 0.40 | 0.14 to 0.16 | 0.12 to 0.16 |
| brain | 0.76 | 0.24 | 0.26 |
| | 0.72 to 0.82 | 0.23 to 0.26 | 0.23 to 0.29 |
| brain/blood | 8.49 | 1.92 | 2.14 |
| | 7.93 to 9.02 | 1.77 to 2.05 | 1.71 to 2.40 |
| heart/blood | 3.96 | 1.16 | 1.10 |
| | 3.44 to 4.25 | 1.09 to 1.24 | 0.88 to 1.28 |

NOTE: The dose of radiotracer injected was 5-7 mCi. Group I was the control, injected with the radiotracer only. Group II included the simultaneous injection of "cold"(dl)-3-HIPP (HCl) (0.53 mg/kg). Group III included the simultaneous injection of (dl) vesamicol (HCl) (0.31 mg/kg). All rats were sacrificed at one hour post-injection.

TABLE 7

Inhibition of (−)-[$^{125}$I]12 accumulation in the rat.

| TISSUE | % dose/g of tissue (range) GROUP I (n = 3) | GROUP II (n = 3) | GROUP III (n = 3) |
|---|---|---|---|
| blood | 0.13 | 0.13 | 0.14 |
| | 0.10 to 0.15 | 0.12 to 0.15 | 0.14 to 0.15 |
| liver | 0.86 | 0.63 | 0.81 |
| | 0.71 to 1.03 | 0.55 to 0.66 | 0.68 to 0.86 |
| lung | 0.92 | 0.57 | 0.73 |
| | 0.79 to 1.13 | 0.48 to 0.68 | 0.66 to 0.85 |
| kidney | 0.98 | 0.46 | 0.46 |
| | 0.96 to 1.02 | 0.43 to 0.50 | 0.43 to 0.49 |
| muscle | 0.15 | 0.10 | 0.13 |
| | 0.13 to 0.16 | 0.09 to 0.13 | 0.11 to 0.16 |
| spleen | 0.83 | 0.36 | 0.50 |
| | 0.64 to 0.94 | 0.30 to 0.41 | 0.46 to 0.54 |

TABLE 7-continued

Inhibition of (−)-[$^{125}$I]12 accumulation in the rat.

| TISSUE | % dose/g of tissue (range) GROUP I (n = 3) | GROUP II (n = 3) | GROUP III (n = 3) |
|---|---|---|---|
| heart | 0.20 | 0.11 | 0.14 |
| | 0.19 to 0.21 | 0.10 to 0.12 | 0.12 to 0.15 |
| brain | 0.64 | 0.15 | 0.20 |
| | 0.61 to 0.67 | 0.14 to 0.16 | 0.19 to 0.22 |
| brain/blood | 5.08 | 1.19 | 1.40 |
| | 4.67 to 1.79 | 1.06 to 1.30 | 1.30 to 1.50 |
| heart/blood | 1.57 | 0.87 | 0.95 |
| | 1.44 to 1.79 | 0.78 to 0.98 | 0.86 to 1.01 |

NOTE: Group I was the control, injected with the radiotracer only. Group II included the simultaneous injection of "cold"(dl)-3-HIPP (HCl) (0.53 mg/kg). Group III included the simultaneous injection of (dl) vesamicol hydrochloride (0.31 mg/kg). The dose of radiotracer was 8-9 μCi. All rats were sacrificed at one hour post-injection.

TABLE 8

Distribution of (+)-[$^{125}$I]13 in the rat (injected dose: 12 uCi).

| TISSUE | % dose/g of tissue (range) TIMEPOINT 5 MIN (n = 3) | 60 MIN (n = 3) | 180 MIN (n = 3) |
|---|---|---|---|
| blood | 0.10 | 0.03 | 0.02 |
| | 0.09 to 0.11 | 0.03 to 0.03 | 0.02 to 0.03 |
| liver | 1.19 | 2.18 | 1.97 |
| | 1.00 to 1.47 | 1.73 to 2.43 | 1.64 to 2.32 |
| lung | 7.87 | 1.77 | 0.62 |
| | 6.37 to 9.75 | 0.82 to 3.16 | 0.57 to 0.70 |
| kidney | 3.12 | 1.86 | 1.53 |
| | 2.80 to 3.51 | 1.37 to 2.33 | 1.40 to 1.59 |
| muscle | 0.33 | 0.14 | 0.13 |
| | 0.18 to 0.43 | 0.12 to 0.15 | 0.12 to 0.16 |
| spleen | 0.92 | 0.90 | 0.77 |
| | 0.69 to 1.33 | 0.77 to 1.08 | 0.69 to 0.81 |
| heart | 1.34 | 0.25 | 0.14 |
| | 0.91 to 1.72 | 0.22 to 0.28 | 0.13 to 0.16 |
| brain | 1.43 | 1.29 | 0.93 |
| | 1.35 to 1.51 | 1.26 to 1.32 | 0.91 to 0.96 |
| Brain: Blood Ratio | 14.8 | 41.7 | 37.4 |
| Heart: Blood Ratio | 13.8 | 8.2 | 5.7 |

TABLE 9

Distribution of (−)-[$^{125}$I]13 in the rat (injected dose: 12 uCi).

| TISSUE | % dose/g of tissue (range) TIMEPOINT 5 MIN (n = 3) | 60 MIN (n = 3) | 180 MIN (n = 3) |
|---|---|---|---|
| blood | 0.13 | 0.06 | 0.06 |
| | 0.10 to 0.16 | 0.06 to 0.07 | 0.05 to 0.07 |
| liver | 1.72 | 1.90 | 0.98 |
| | 1.21 to 2.12 | 1.55 to 2.02 | 0.83 to 1.12 |
| lung | 5.05 | 0.54 | 0.24 |
| | 3.96 to 5.73 | 0.45 to 0.60 | 0.22 to 0.27 |
| kidney | 3.38 | 1.47 | 0.74 |
| | 2.97 to 3.59 | 1.23 to 1.68 | 0.65 to 0.88 |
| muscle | 0.32 | 0.11 | 0.05 |
| | 0.25 to 0.34 | 0.09 to 0.11 | 0.05 to 0.06 |
| spleen | 0.70 | 0.57 | 0.23 |
| | 0.50 to 0.96 | 0.51 to 0.63 | 0.21 to 0.24 |
| heart | 0.77 | 0.13 | 0.05 |
| | 0.70 to 0.88 | 0.12 to 0.14 | 0.05 to 0.06 |
| brain | 1.08 | .70 | 0.35 |
| | 0.86 | 0.59 to 0.82 | 0.33 to 0.36 |
| Brain: Blood Ratio | 8.7 | 11.1 | 5.5 |
| Heart: Blood Ratio | 6.2 | 2.0 | 0.9 |

TABLE 10

Inhibition of (+)- and (−)-[$^{125}$I]13 accumulation in the rat

| TISSUE | GROUP I (n = 3) | GROUP II (n = 3) | GROUP III (n = 3) | GROUP IV (n = 3) |
|---|---|---|---|---|
| | % dose/g of tissue (range) | | | |
| blood | 0.05 | 0.03 | 0.10 | 0.08 |
| | 0.05 to 0.06 | 0.03 to 0.04 | 0.08 to 0.15 | 0.07 to 0.09 |
| liver | 1.85 | 2.53 | 1.66 | 1.44 |
| | 1.73 to 2.01 | 2.33 to 2.82 | 1.44 to 1.89 | 1.38 to 1.5[illegible] |
| lung | 1.01 | 0.42 | 0.66 | 0.34 |
| | 0.87 to 1.27 | 0.35 to 0.57 | 0.60 to 0.76 | 0.28 to 0.41 |
| kidney | 1.87 | 0.41 | 1.26 | 0.38 |
| | 1.82 to 1.95 | 0.27 to 0.55 | 1.13 to 1.45 | 0.33 to 0.44 |
| muscle | 0.14 | 0.06 | 0.11 | 0.07 |
| | 0.11 to 0.17 | 0.04 to 0.09 | 0.09 to 0.14 | 0.06 to 0.08 |
| spleen | 0.88 | 0.33 | 0.61 | 0.27 |
| | 0.78 to 1.00 | 0.29 to 0.36 | 0.57 to 0.66 | 0.24 to 0.29 |
| heart | 0.22 | 0.08 | 0.13 | 0.08 |
| | 0.19 to 0.24 | 0.07 to 0.10 | 0.10 to 0.16 | 0.07 to 0.09 |
| brain | 0.87 | 0.24 | 0.73 | 0.13 |
| | 0.74 to 1.00 | 0.20 to 0.27 | 0.67 to 0.82 | 0.11 to 0.1[illegible] |
| brain/ | 17.86 | 7.02 | 7.41 | 1.61 |
| blood | 15.95 to 21.09 | 6.37 to 7.38 | 5.75 to 8.46 | 1.41 to 1.88 |
| heart/ | 4.41 | 2.48 | 1.31 | 0.99 |
| blood | 4.31 to 4.58 | 2.09 to 2.90 | 1.06 to 1.56 | 0.92 to 1.13 |

NOTE: Group I received (+)-[$^{125}$I]13 only. Group II received the (+) radiotracer co-injected with 0.31 mg/kg (dl)vesamicol hydrochloride. Group III received (−)-[$^{125}$I]13 only. Group IV received the (−) radiotracer co-injected with 0.31 mg/kg (dl)vesamicol hydrochloride. All animals were sacrificed at one hour post-injection. The dose of radiotracer injected per animal was 8-9 uCi.

Chemistry

Figure 7:
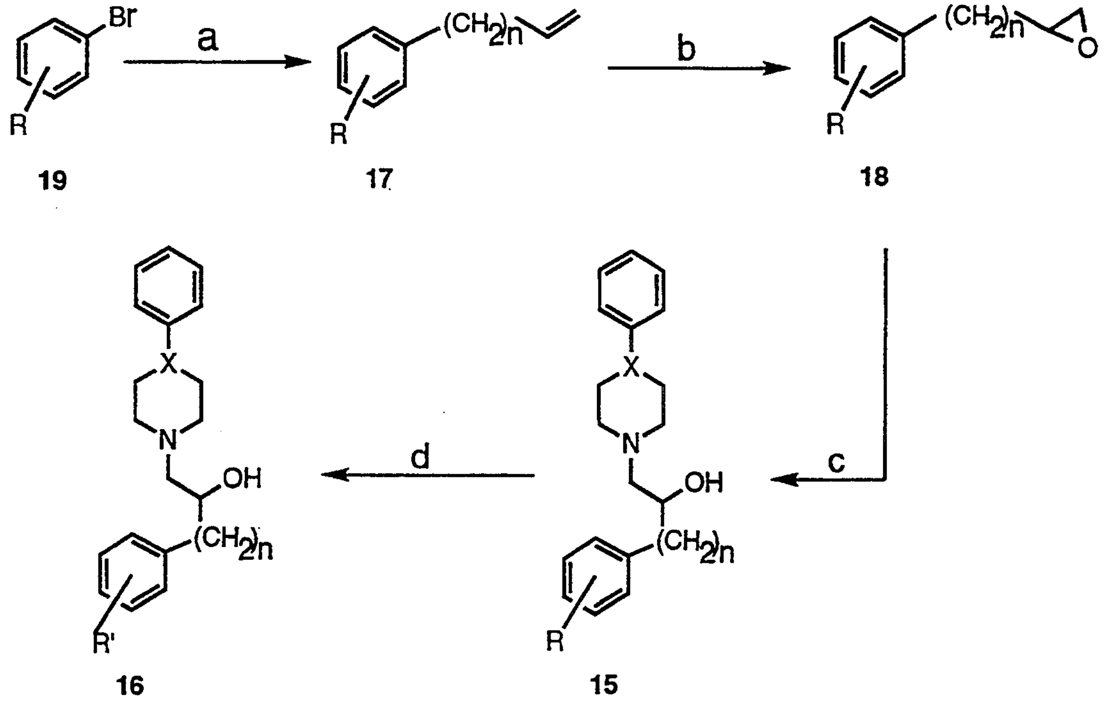
FIG. 7 shows a scheme for preparing compounds 15 and 16.
Figure 8:
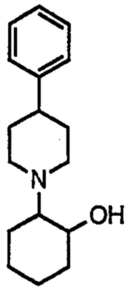
FIG. 8 shows additional anticholinergics of the invention.
Figure 8:
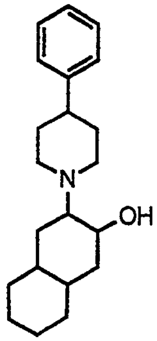
Figure 8:
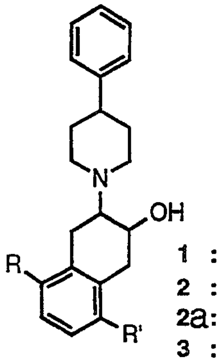
Figure 8:
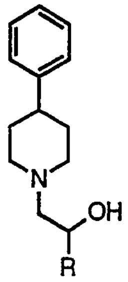
Figure 8:
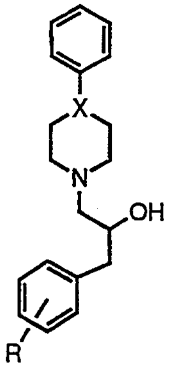
Figure 8:
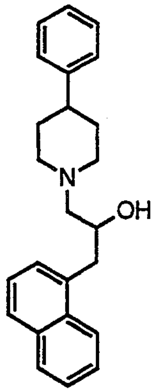
Figure 8:
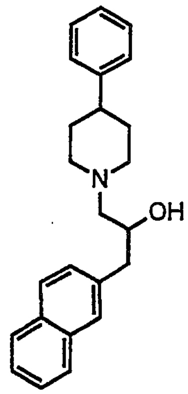
Figure 8:
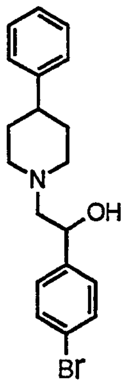

The target compounds 15*a-j* (see FIG. 8) were obtained from the corresponding alkenes via expoxidation and subsequent reaction with 4-phenylpiperidine (FIG. 7). The yields for this two-step sequence range between 50 and 80 percent. The alkene precursors were obtained by reaction of allyl bromide with the corresponding Grignard reagent prepared in situ. The substituted ethanol, 15*i*, was obtained from 4-bromostyrene, following the sequence outlined in FIG. 7. Finally, the phenols 16*a* and 16*b*, were obtained by dealkylation of the corresponding anisoles. All target compounds were found to be homogeneous on HPLC, although some of these samples were not analytically pure. The assignment of structure for the target aminoalcohols is based on the preferential attack of the secondary amine at the less hindered carbon of the epoxide. In the NMR spectrum of 15*b*, the methine proton at the C2 position of the propyl fragment appears as a multiplet at 3.92. On acetylation ($Ac_2O$, $Et_3N$) the signal shifts to 5.25 (confirming the assignment of structure). The racemate 15*a* was successfully resolved by fractional crystallization of the diastereomeric tartrates to yield (+)-15*a* and (−)-15*a* in 97% and 92% ee, respectively (as determined by HPLC).

A reexamination of the data indicated a) that although the ethanol analog 4 was a very weak inhibitor of vesicular acetylcholine storage, and b) the addition of an α-methyl group, to yield 14*b*, resulted in a thirty-fold increase in activity. Based on the totality of available evidence we suggested: 1) that the minimum bioactive fragment at the vesamicol receptor was represented by the substituted ethanol 4, 2) that the region of the binding site which accommodates the cyclohexyl (or fused bicyclic) moiety is characterized by a minimum steric bulk requirement, and 3) that this requirement may be satisfied by bulky groups linked to the hydroxyl-containing acyclic fragment (as in 15*a* and its analogs). The biological data obtained in the present study supports these propositions.

Although none of these new compounds contain the cyclohexyl ring, some are nevertheless fairly potent ligands for the vesamicol receptor (Table 11). The levorotary isomer (−)-15*a*, a structural mimic of benzovesamicol, 1*a*, is essentially equipotent with vesamicol. In spite of the inherent flexibility of 15*a*, receptor binding is stereoselective, the levorotatory isomer being more potent than its corresponding antipode. Since the cyclohexyl-containing analogs such as 2 and 3, exhibit a similar levo/dextro enantioselectivity, 15*a* and its analogs would appear to be suitable mimics of benzovesamicol.

The binding data also reveals a number of other trends. Replacement of the piperidyl fragment with a piperazyl moiety is accompanied by significant reductions in binding affinity (15*a* vs 15*e* and 15*b* vs 15*f*). This observation is consistent with an earlier report on vesamicol analogs. On the whole, most single-point substitutions on the pendant phenyl ring appear to have only minimal effects on binding affinity. Halogen substitution at the meta position is preferred over the para position (15*b* and (15*j* and 15*a* ). In contrast, hydrophilic substituents are better tolerated at the para position (16*a* vs 16*b*). The presence of a second fused ring results in variable effects on binding to the vesamicol receptor. Although the β-naphthyl analog 15*h* is essentially equipotent with 15*a* , the corresponding α-naphthyl isomer (15*h* is substantially less potent. The differential affinity of these isomeric naphthalenes, which may be partly attributed to the rigidity of the fused bicyclic system, suggests a preferred orientation for bulky substituents in this region of the receptor site. Interestingly, racemic 15*i* is equipotent with (dl)-vesamicol.

Experimental

General: Synthetic intermediates were purchased form Aldrich, Inc. (Milwaukee, Wis.), and were used as received. Solvents were distilled immediately prior to use. Commercially available reagents were used without subsequent purification.

All air-sensitive reactions were carried out under nitrogen. Standard handling techniques for air-sensitive materials were employed throughout this study. Melting points were determined on a Mel-Temp melting point apparatus and are uncorrected. The specific rotation was determined on an automatic polarimeter (Autopol III, Rudolph Research, Flanders, N. J.). $^1$H NMR spectra were recorded on an IBM-Brucker spectrometer at 200 MHz. NMR spectra are referenced to the deuterium lock frequency of the spectrometer. Under these conditions, the chemical shifts (in ppm) of residual solvent in the $^1$H NMR spectra was found to be respectively; $CHCl_3$, 7.26; DMSO, 2.56; HOD, 4.81. The following abbreviations are used to describe peal patterns when appropriate: b=broad, s =singlet, d=doublet, t=triplet, q=quartet, m=multiplet. Both low and high resolution MS were performed on an AEI MS-30 instrument. Elemental analyses were performed by Atlantic Microlab, Inc., Norcross, Ga.

Column chromatography was performed using "Baker Analyzed" silica gel (60-200 mesh). Preparative chromatography was performed on either a Harrison Research Chromatotron using Merck 60 $PF_{254}$ silica gel or a preparative HPLC (Rainin Instrument Co.) using a 41.1 mm ID Dynamax silica gel column (at a solvent delivery rate of 80 ml/min.) Enantiomeric purity was determined by HPLC with a Chiralcel OD column (isopropyl alcohol: hexane: $ET_3N$, 10:89:I; flow rate 1 ml/min.). Analytical TLC was performed on Analtech glass TLC plates coated with silica gel GHLF and were visualized with UV light and or methanolic iodine. All target compounds were checked for purity by HPLC (silica gel, 10–20% isopropyl alcohol-hexanes, trace $Et_3N$). Representative procedures for the steps shown on Scheme I are provided below as Procedures A–D.

Procedure A

2-[3-(1-Propenyl)]naphthalene, **17*h* (Compound 17*h***)

Allyl bromide (4.8 mL, 55 mmol) in THF (25 mL) was added to a solution of the Grignard reagent prepared by adding 2-bromonaphthalene (7.0 mL, 50 mmol) in THF (25 mL) to a suspension of magnesium (1.2 g, 50 mmol) in THF (50 mL). Reaction conditions and work up are similar to those described above for the isomeric propene. The residue obtained after work up was distilled (86° C./1.4 torr) to give 6.1 g (75.0%) of colorless oil. $^1H$ NMR ($CDCl_3$) δ3.68 (d, 2H, J=6.57 Hz), 5.24 (m, 1H), 5.32 (m, 1H, 6.20 (m, 1H), 7.53 (m, 3H), 7.76 (s, 1H), 7.93 (m, 3H). CIMS ($NH_3$) m/e (intensity) 170.2 ((M+2H)−100.0).

Procedure B

2-[3-(1,2 Epoxy)propyl]naphthalene, **18*h*, (Compound 18*h***),

A solution of 2-[3-(1-propenyl)]naphthalene (5.9 g, 35 mmol) in $CH_2Cl_2$ (200 mL) was cooled in an ice bath. mCPBA (50%, 13.3 g, 38.5 mmol) was added in small portions over 5 minutes. The solution was allowed to come to room temperature, stirred for 16 hrs, and subsequently concentrated under reduced pressure. The residue was triturated with $CCl_4$ and filtered to remove m-chlorobenzoic acid. The flitrate was washed with 1:1 5% $NaHSO_3$:5% $NaHCO_3$ (100 mL). The aqueous layer was subsequently washed with $CCl_4$ (2×100 mL). The combined organic layers were dried over $Na_2SO_4$, filtered and concentrated under reduced pressure to give 6.7 g (quantitative) of a yellow oil which was carried on without further purification. $^1H$ NMR ($CDCl_3$) δ2.62 (dd, 1 H, J=2.7 Hz, J'=5.0 Hz) 2.85 (m, 1H), 3.06 (m, 2H), 3.27 (m, 1H), 7.48 (m, 3H) 7.74 (s, 1H), 7.85 (m, 2H). CIMS ($NH_3$) m/e (intensity) 185.9 ((M+2H)−, 100.00).

Procedure C (±)-1-[1-(4-Phenylpiperidinyl)]-2-hydroxy-3-(2-naphthyl)propane, **15*h* (Compound 15*h***)

2-[3-(1,2-Epoxy)propyl]naphthalene (2.8 g, 15 mmol), **18*h*** and 4-phenylpiperidine (2.4 g, 15 mmol) were dissolved in EtOH (30 ml) and refluxed for 3 hours. The solution was concentrated under reduced pressure and the residue was purified by HPLC on $SiO_2$ (9:1 hexane:i-PrOH+1% $Et_3N$). The desired fractions were collected and concentrated under reduced pressure to give 10.4 g (80%) of a dark yellow oil. The hydrochloride was prepared by treating an ethanolic solution of the amine with HCl gas and precipitating out the salt with $Et_2O$ to give off-white cubic crystals (mp 213°–15° C.). $^1H$ NMR ($d_6$-DMSO) δ1.89 (m, 2H), 2.16 (m, 2H), 2.78 (m, 1H), 2.95 (d, 2H, J=6.05 Hz), 3.14 (m, 2H), 3.47 (b-s, 2H), 3.63 (m, 2H), 4.47 (m, 1H), 5.81 (b-s, 1H), 7.29 (m, 5H), 7.49 (m, 3H), 7.86 (m, 4H), 10.33 (b-s, 1H). Anal. calcd for $C_{24}H_{27}NO.HCl$: C, 75.47; N, 3.67. Found: C, 75.44; H, 7.41; N, 3.70.

3-(4-Bromophenyl)-2-hydroxy-1-[1-(4-phenylpiperidinyl)]propane, **15*a* (Compound 15*a*** ).

Compound **17*a* was prepared in 80% yield as previously described. Starting with 4.0 g (20 mmol) of 17*a* the crude epoxide 18*a* was obtained, according to Procedure A, in 83% yield. The latter was reacted with 2.42 g (15 mmol) of 4-phenylpiperidine (Procedure B) to yield, after chromatography 2.7 g (48%) of crystalline 15*a***. $^1H$ NMR ($CDCl_3$) δ1.65 (m, 4H), 2.01 (t, 1H), 2.32–2.93 (m, 7H), 3.08 (d, 1H), 3.78 (br s, 1H), 3.92 (m, 1H), 7.13–7.36 (m, 7H), 7.46 (d, 2H). The hydrochloride was obtained as described in Procedure C, as a white solid; mp 194°–198° C. Anal. ($C_{20}H_{24}BrNO.HCl$) C, H. N.

3-(3-Bromophenyl)-2-hydroxy-1-[1-(4-phenylpiperidinyl)]propane, **15*b* (Compound 15*b***).

Following Kugelrohr distillation (50°–80° C., 0.3 mm Hg), compound **17*b*was obtained as a colorless liquid in 87% yield from 1,3-dibromobenzene (Procedure A). $^1H$ NMR ($CDCl_3$) δ3.42 (m, 2H), 5.15 (m, 2H), 6.00 (m, 1H), 7.28 (m, 4H), Compound 15*b*** was obtained as a white crystalline hydrochloride in 35%, after two steps (Procedure B and C); mp 161°–163° C. $^1H$ NMR (DMSO-$d_6$) δ1.90 (m, 2H), 2.16 (m, 2H), 2.78 (m, 2H), 3.10 (m, 4H), 3.38 (br s, 1H), 3.63 (m, 2H), 4.35 (br s, 1H), 5.72 (m, 1H), 7.37 (m, 9H), 10.30 (br s, 1H). Anal. ($C_{20}H_{24}BrNO.HCl$): calcd.: C, 58.48; H, 6.13; N, 3.41. Found: C, 60.27; H, 6.41; N, 3.50.

2-Hydroxy-3-(4-methoxyphenyl)-1-(4-phenylpiperidinyl)propane, **15*c* (Compound 15*c***).

Starting with 4-bromoanisole (15.0 g, 80 mmol), Procedure A yielded 9.0 g (76%) of the colorless oil **17*c***. $^1H$ NMR ($CDCl_3$) δ3.41 (d, 2H), 3.82 (s, 3H), 506–5.16 (m, 2H), 5.90–6.10 (m, 1H), 6.88 (d, 2H, J=8.6 Hz), 7.15 (d, 2H, J=8.6 Hz).

The product **17*c* was subjected to Procedure B to yield the epoxide 18*c*** as a colorless liquid (6.5 g, 79%). $^1H$ NMR ($CDCl_3$) δ2.50–3.16 (m, 5H), 3.78 (s, 3H), 6.85 (d, 2H, J=8.6 Hz), 7.17 (d, 2H, J=8.61 Hz).

Compound **18*c* was reacted with 4-phenylpiperidine (Procedure C) to yield 3.0 g (42%) of the hydrochloride (15*c***; mp 207.1° C. $^1H$ NMR (DMSO-$d_6$) δ1.93–3.04 (m, 9H), 3.58 (d, 4H, J=11.0 Hz), 3.73 (s, 3H), 4.29 (br s, 1H), 5.66 (d, 1H, J=5.1 Hz), 6.85–7.37 (m, 9H). Anal. ($C_{21}H_{27}NO_2.HCl$) calcd. :C, 69.69; H, 7.80; N, 3.87. Found: C, 69.73; H, 7.81; N, 3.95.

2-Hydroxy-3-(3-methoxyphenyl)-1-(4-phenylpiperidinyl)propane, **15*d* (Compound 15*d*) 3-(3-Methoxyphenyl)propene, 17*d***, was obtained from 3-bromoanisole, according to Procedure A, in 85% yield. $^1H$ NMR ($CDCl_3$) δ3.44 (d, 2H, J=6.7Hz), 3.85 (s, 3H), 5.13–5.29 (m, 2H), 5.94–6.15 (m, 1H), 6.81–7.33 (m, 4H).

The epoxide **18*d* was subsequently obtained in 80% yield from 17*d*** (Procedure B). $^1H$ NMR ($CDCl^3$) δ2.54–3.27 (m, 5H), 3.80 (s, 3H), 6.76–7.27 (m, 4H).

The target hydrochloride **15*d*** was finally obtained as a white solid, following Procedure C, in 33% yield; mp 180° C. (isopropyl alcohol). $^1H$ NMR (DMSO-$d_6$) δ1.93–3.07 (m, 9H), 3.60 (d, 2H, J=13.0 Hz), 3.75 (s, 3H), 4.32 (br s, 1H), 5.87 (br s, 1H), 6.74–7.27 (m, 9H), 10.06 (br s, $^1H$). Anal. ($C_{21}H_{27}NO_2.HCl$) calcd: C, 69.69; H, 7.80; N, 3.87, Found: C, 69.48; H, 7.81; N, 3.92.

3-(4-Bromophenyl)-2-hydroxy-1-(4-phenylpiperazinyl)-propane, **15*e* (Compound 15*e***).

The reaction of **18*a* a with 1-phenylpiperazine, as described in Procedure C, provided the white crystalline hydrochloride 15*e*** in 13% yield. mp 235.5° C. $^1H$ NMR (DMSO-$d_6$) δ2.73 (t, 2H, J=5.7 Hz), 3.16–3.25 (m, 6H), 3.62–3.76 (m, 4H), 4.31 (br s, 1H), 6.87 (t, 1H, J=7.2 Hz, 7.01 (d, 2H, J=8.0 Hz), 7.26 (m, 4H), 7.58 (d, 2H), 7.94 (br s, 2H). Anal. ($C_{19}H_{23}BrN_2O.HCl$) calcd: C, 50.91; H, 5.62; N, 6.25. Found: C, 51.48; H, 5.69; N, 6.31.

3-(3-Bromophenyl)-2-hydroxy-1-(4-phenylpiperazinyl)-propane, **15*f* (Compound 15*f***).

1-Phenylpiperazine and epoxide **18*d* were reacted (Procedure C) to yield the white crystalline hydrochloride 15*f*** in 13% yield; mp 21 6.9° C. $^1$H NMR (DMSO-$d_6$) δ5 2.73 (t, 2H, J=5.7 Hz), 3.16–3.25 (m, 6H), 3.62–3.76 (m, 4H), 4.35 (br s, 1H), J=7.2 Hz), 7.04 (d, 2H, J=8.1 Hz), 7.28 (m, 4H), 7.40–7.51 (m, 2H), 8.73 (br s, 2H). Anal. ($C_{19}H_{23}BrN_2O$. HCl) calcd: C, 50.91. H, 5.62; N, 6.25. Found: C, 51.95; H, 5.69; N, 6.22.

2-Hydroxy-3-(2-naphthyl)-1-(4-phenylpiperidinyl)propane, **15*g*, (Compound 15*g***).

The reaction of 2-bromonaphthalene, **19*g*, and allyl bromide (Procedure A) yielded 17*g***, as a colorless liquid, in 75% yield; bp 86° C. (1.5 mm Hg). $^1$H NMR ($CDCl_3$) δ3.68 (d, 2H, J=6.6 Hz), 5.24 (m, 1H), 5.32 (m, 1H), 6.20 (m, 1H), 7.53 (m, 3H), 7.76 (s, 1H), 7.93 (m, 3H). CIMS ($NH_3$) m/e (intensity) 170.2 ($M+2H^+$, 100.0).

The arylalkene **17*g* was subjected to Procedure B to provide a quantitative yield of the yellow liquid epoxide 18*g*** g. $^1$H NMR ($CDCl_3$) δ2.62 (dd, $^1$H, J=2.7 Hz, J'=5.0 Hz), 2.85 (m, 1H), 3.06 (m, 2H), 3.27 (m, 1H), 7.48 (m, 3H), 7.74 (s, 1H), 7.85 (m, 2H). CIMS ($NH_3$) m/e (intensity) 185.9 ($M+2H^+$, 100.0).

The hydrochloride **15*g*** was obtained, as a white crystalline solid, in 80% (Procedure C); mp 213–215° C. $^1$H NMR (DMSO-$d_6$) δ1.89 (m, 2H), 2.16 (m, 2H), 2.78 (m, 1H), 2.95 (d, 2H, J=6.0 Hz), 3.14 (m, 2H), 3.47 (br s, 2H), 3.63 (m, 2H), 4.47 (m, 1H), 5.81 (br s, 1H), 7.29 (m, 5H), 7.49 (m, 3H), 7.86 (m, 4H), 10.33 (br s, 1H). Anal. ($C_{24}H_{27}NO.HCl$) calcd.: C, 75.47; H, 7.40; N, 3.67. Found: C, 75.57; H, 7.41; N, 3.65.

(dl)-1-(4-Bromophenyl)-2-(4-phenylpiperidinyl)ethanol. **15*i*, (Compound 15*i***).

Compound **15*i*** was obtained from the epoxidation of 4-bromostyrene and subsequent reaction of the epoxide with 4-phenylpiperidine in ethanol (Procedure B and C). The product was purified by HPLC (20% isopropyl alcohol-hexanes, trace $Et_3N$; silica gel) to yield a white solid (48%). $^1$H NMR ($CDCl_3$) δ1.86 (m, 4H); 2.17 (t, 1H), 2.37–2.55 (m, 4H), 2.93 (d, 1H), 3.26 (d, 1H), 4.26 (br s, 1H), 4.72 (dd, 1H), 7.22–7.36 (m, 7H), 7.48 (d, 2H). The hydrochloride was recrystallized from isopropyl alcohol, mp 233°–236° C. Anal. ($C_{19}H_{22}BrNO.HCl$) calcd: C, 57.66; H, 5.85; N, 3.54. Found: C, 56.47; H, 6.04; N, 3.43.

Procedure D

2-Hydroxy-3-(4-hydroxyphenyl)-1-(4-phenylpiperidinyl)propane, **16*a* (Compound 16*a*) Compound 15*c* (1.0 g, 3.1 mmol) was dissolved in 60 ml of dry $CH_2Cl_2$ and the solution was cooled to −60° C. (Dry Ice-acetone-$CCl_4$). A 1M solution of $BBr_3$ (3.82 ml) was then added dropwise under nitrogen, while maintaining the temperature of −60° C. After 1 hour the reaction mixture was allowed to warm up to room temperature and stirred for an additional 12 hours. The reaction mixture was subsequently treated with 10 ml of MeOH and concentrated under reduced pressure. The residue was diluted with 10% aq. NaOH (100 ml) and extracted with EtOAc (150 ml). The product was converted into the corresponding hydrochloride by bubbling HCl(g) into this solution. The precipitated salt was finally recrystallized from isopropyl alcohol to yield 0.8 g (75%) of 16*a***; mp 216.5° C. $^1$H NMR (DMSO-$d_6$) δ1.85–3.63 (m, 14H), 4.24 (br s, 1H), 5.65 (br s, 1H), 6.73 (d, 2H, J=8.3 Hz), 7.05 (d, 2H, J=8.3 Hz), 7.21–7.36 (m, 5H), 9.40 (s, 1H), 10.18 (br s, 1H). Anal. ($C_{20}H_{25}NO_2.HCl$) calcd: C, 69.05; H, 7.53; N, 4.03. Found: C, 68.62; H, 7.79; N, 4.13.

2-Hydroxy-3-(3-hydroxyphenyl)-1-(4-phenylpiperidinyl)propane, **16*b*, (Compound 16*b***).

Starting with 0.85 g (2.2 mmol) of **15*d*, the demethylation was carried out, according to Procedure D to yield 0.35 (46%) g the hydrochloride 16*b***, mp 216.5° C. $^1$H NMR (DMSO-$d_6$) δ1.94–3.61 (m, 14H), 4.25 (br s, 1H), 5.68 (d, 1H, J=5.2 Hz), 6.63–7.33 (m, 9H), 9.41 (s, 1H), 9.98 (br s, 1H). Anal. calcd. for $C_{20}H_{25}NO_2$. HCl: C, 69.05; H, 7.53; N, 4.03. Found: C, 68.41; H, 7.58; N, 4.02.

Biological

The compounds were evaluated in a purified preparation of cholinergic synaptic vesicles isolated from the electric organ of Torpedo californica. A full description of this assay was described earlier. However, the present study was carried out in the absence of ATP and acetylcholine. The data reported are averages of duplicates which exhibit a relative range of less than 5%. Nonlinear regression analysis was carried out with MINSQ (MicroMath Scientific Software, Salt Lake City, Utah.). Protein content was determined by the method of Bradford, using a bovine serum albumin standard.

TABLE 11

Binding affinities of aminoalcohols at the vesamicol receptor[a].

| Compound[c] | n | R | R' | X | $K_d$(nM) |
|---|---|---|---|---|---|
| [b](dl)-Vesamicol | — | — | — | — | 34 ± 6 |
| (+)-15a | 1 | p-Br | — | CH | 328 ± 108 |
| (−)-15a | 1 | p-Br | — | CH | 36 ± 5 |
| (dl)-15a | 1 | p-Br | — | CH | 170 ± 20 |
| 15b | 1 | m-Br | — | CH | 73 ± 17 |
| 15c | 1 | p-OMe | — | CH | ND |
| 15d | 1 | m-OMe | — | CH | 115 ± 14 |
| 15e | 1 | p-Br | — | N | 1540 ± 260 |
| 15f | 1 | m-Br | — | N | 990 ± 102 |
| 15g | 1 | 2,3-benzo | — | CH | 1400 ± 300 |
| 15h | 1 | 3,4-benzo | — | CH | 145 ± 15 |
| 15i | 0 | p-Br | — | CH | 30 ± 5 |
| 15j | 1 | m-I | — | CH | 73 ± 11 |
| 16a | 1 | — | p-OH | CH | 220 ± 54 |
| 16b | 1 | — | m-OH | CH | 520 ± 30 |

[a]The compounds were tested as the corresponding hydrochlorides, using highly purified synaptic vesicles obtained from the electric organ of Torpedo Californica, following a procedure described earlier (8).
[b]Data obtained form Ref. 4.
[c]See general structure in FIG. 7

Alternative Compounds

The work above has shown that a minimum recognizable structure to the vesamicol receptor is:

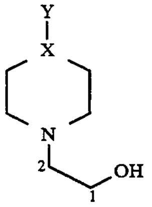

That minimum recognizable structure is then modified by adding a hydrophobic moiety to either or both carbon atoms (number 1 and 2 above) of the ethanol fragment. Closed chain groups should not be used to avoid manufacture and separation problems.

Generally, the anticholinergics of the invention include the following:

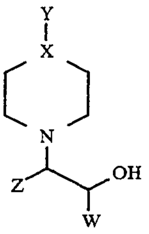

wherein

X is CH, N;

Y is an aromatic, heteroaromatic or alicyclic group;

Z is H, or an alkyl, arylalkyl, heteroarylalkyl, aroylalkyl, heteroaroylalkyl, cycloalkyl, or aryl group and such groups including halogen substitutions;

W is H, or an alkyl, arylalkyl, heteroarylalkyl, aroylalkyl, heteroaroylalkyl, cycloalkyl, or aryl group and such groups including halogen substitutions; and Z or W may have chemically bound thereto a transition metal or other radiomarker.

Figure 1:
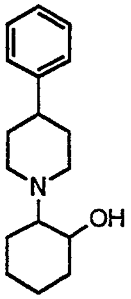
FIG. 1 shows vesamicol and analogs.
Figure 1:
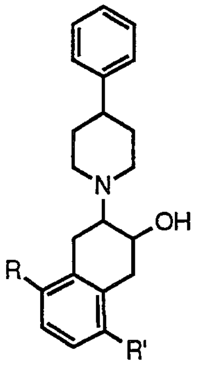
Figure 1:
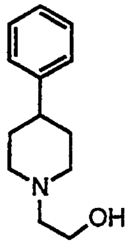
Figure 1:
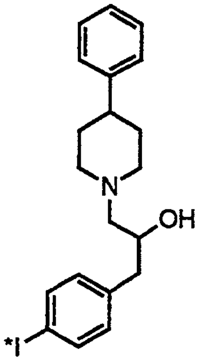
Figure 1:
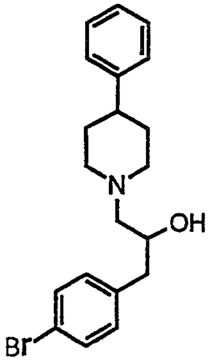
Figure 1:
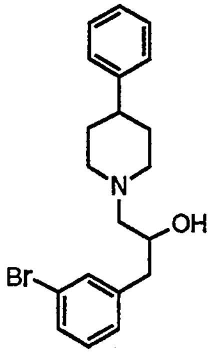
Figure 1:
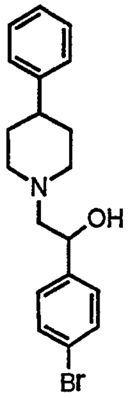
Figure 1:
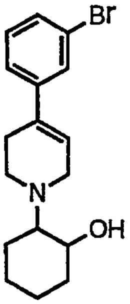
Figure 1:
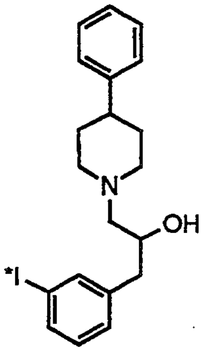
Figure 1:
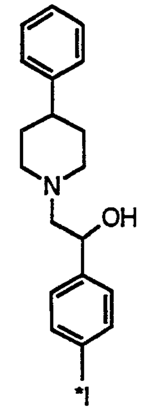
Figure 2:
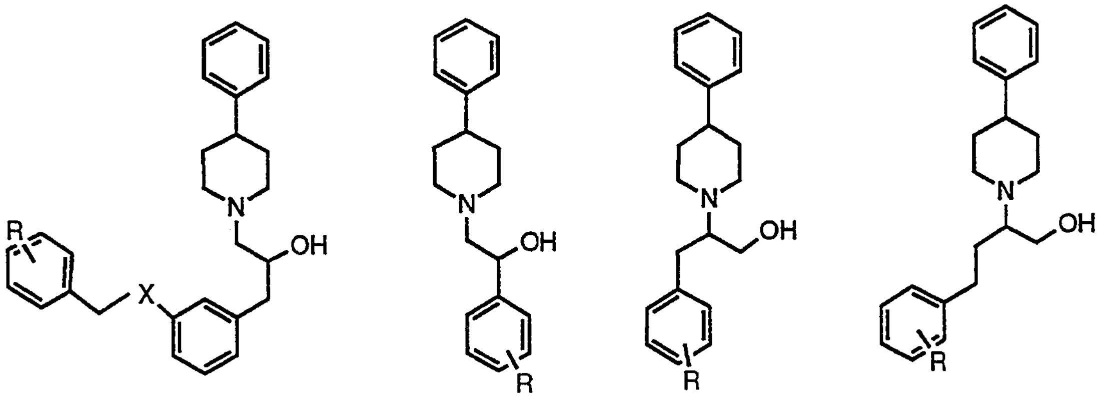
FIG. 2 shows structural skeletons of proposed compounds.

FIG. 2 shows other possible compositions which should be effective anticholinergics in accordance with the teachings of this invention.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. Unless otherwise indicated, all parts and percentages are by weight.

This completes the description of the preferred and alternate embodiments of the invention. Those skilled in the art may recognize other equivalents to the specific embodiment described herein which equivalents are intended to be encompassed by the claims attached hereto.

What is claimed is:

1. A radiopharmaceutical for binding to a vesamicol receptor for mapping cholinergic innervation in the brain comprising a chemical with the structural formula:

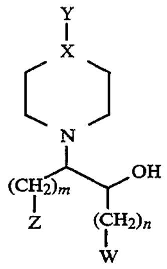

wherein

X is CH, N;

m is 0 to 5;

n is 0 to 3;

Y is a phenyl group;

Z is H, or a phenyl, fused bicyclic, naphthyl, thiophene or pyrrol group;

W is H, or a phenyl, fused bicyclic, naphthyl, thiophene or pyrrol group; and further characterized in that both Z and W cannot be H, and Z or W includes a radionuclide of iodine or a transition metal radionuclide joined chemically thereto.

2. The radiopharmaceutical of claim 1 wherein said transition element is Technetium-99 m.

3. A method for monitoring cholinergic innervation in a living brain. which comprises injecting a subject with an effective amount of a radiolabeled compound of the structural formula:

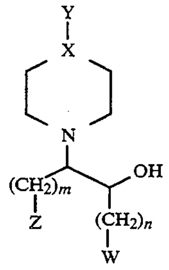

wherein

X is CH, N;

m is 0 to 5;

n is 0 to 3;

Y is a phenyl group;

Z is H, or a phenyl, thiophene, fused bicyclic, naphthyl or pyrrol group;

W is H, or a phenyl, thiophene, fused bicyclic naphthyl or pyrrol group: and further characterized in that both Z and W cannot be H, and Z or W include a radiolabel attached chemically thereto, said radiolabel being a pharmacologically inert radioisotope capable of detection using a photoscanning device: and subsequently scanning with said device to detect cholinergic innervation.

4. An anticholinergic composition comprising a chemical with the structural formula:

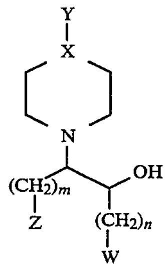

wherein

X is CH, N;

m is 0 to 5;

n is 0 to 3;

Y is a phenyl group;

Z is H, or a phenyl, thiophene, fused bicyclic, naphthyl or pyrrol group:

W is H, or a phenyl, thiophene, fused bicyclic, naphthyl or pyrrol group; and further characterized in that both Z and W cannot be H, and Z or W include a radiolabel joined thereto.

5. A radiopharmaceutical for bonding to the vesamicol receptor for mapping cholinergic innervation in the brain comprising a chemical with the structural formula:

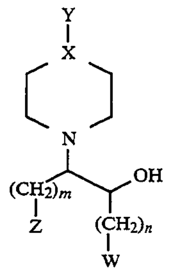

wherein

X is CH, N;

m is 0 to 5;

n is 0 to 3;

Y is a phenyl, thiophene or fused bicyclic group;

Z is H;

W is a phenyl, fused bicyclic, naphthyl, thiophene or pyrrol group; and further characterized in that W includes a radionuclide of iodine or a transition metal radionuclide joined chemically thereto.

6. The radiopharmaceutical of claim 5 wherein Y is a phenyl group, m is 0 and n is 0.

* * * * *

UNITED STATES PATENT AND TRADEMARK OFFICE

CERTIFICATE OF CORRECTION

PATENT NO. : 5,358,712

DATED : October 25, 1994

INVENTOR(S) : Efange et al

It is certified that error appears in the above-indentified patent and that said Letters Patent is hereby corrected as shown below:

Col. 5, line 67, add $\mu$ between 1 and m.
Col. 9, line 37, delete Z, insert 7.
Col. 21, line 6, delete d, insert b.
Col. 21, line 25, delete the second g.

Signed and Sealed this

Second Day of May, 1995

Attest:

BRUCE LEHMAN

*Attesting Officer*

*Commissioner of Patents and Trademarks*